United States Patent [19]
Leahy et al.

[11] Patent Number: 6,090,045
[45] Date of Patent: Jul. 18, 2000

[54] EXPERT SYSTEM SOFT TISSUE ACTIVE MOTION TECHNIQUE FOR RELEASE OF ADHESIONS AND ASSOCIATED APPARATUS FOR FACILITATING SPECIFIC TREATMENT MODALITIES

[76] Inventors: P. Michael Leahy, 8615 Chapel Square Ct., Colorado Springs, Colo. 80920; Tim Patterson, 4865 Langdale Way, Colorado Springs, Colo. 80906

[21] Appl. No.: 08/807,792

[22] Filed: Feb. 28, 1997

[51] Int. Cl.[7] .................... G06F 159/00; A61B 19/00
[52] U.S. Cl. ................................ 600/301; 128/898
[58] Field of Search ............... 600/301; 128/898

[56] References Cited

U.S. PATENT DOCUMENTS

| | | | |
|---|---|---|---|
| 4,290,114 | 9/1981 | Sinay | 364/900 |
| 5,085,208 | 2/1992 | Massaro | 128/67 |
| 5,231,977 | 8/1993 | Graston | 128/24 |
| 5,501,657 | 3/1996 | Feero | 601/40 |

FOREIGN PATENT DOCUMENTS

| | | | |
|---|---|---|---|
| 2 218 546 | 11/1989 | United Kingdom | G06F 15/42 |

*Primary Examiner*—David J. Isabella
*Attorney, Agent, or Firm*—Duft, Graziano & Forest, P.C.; Dan Cleveland, Jr., Esq.

[57] ABSTRACT

A method for the non-surgical treatment of soft tissue lesions includes placing a contact point near the lesion and causing the patient to move in a manner that produces a longitudinal sliding motion of soft tissues, e.g., nerves, ligaments, and muscles, beneath the contact point. Treatments are continued at sequential time intervals until the symptoms produced by the lesions are alleviated.

7 Claims, 31 Drawing Sheets

Microfiche Appendix Included
(3 Microfiche, 252 Pages)

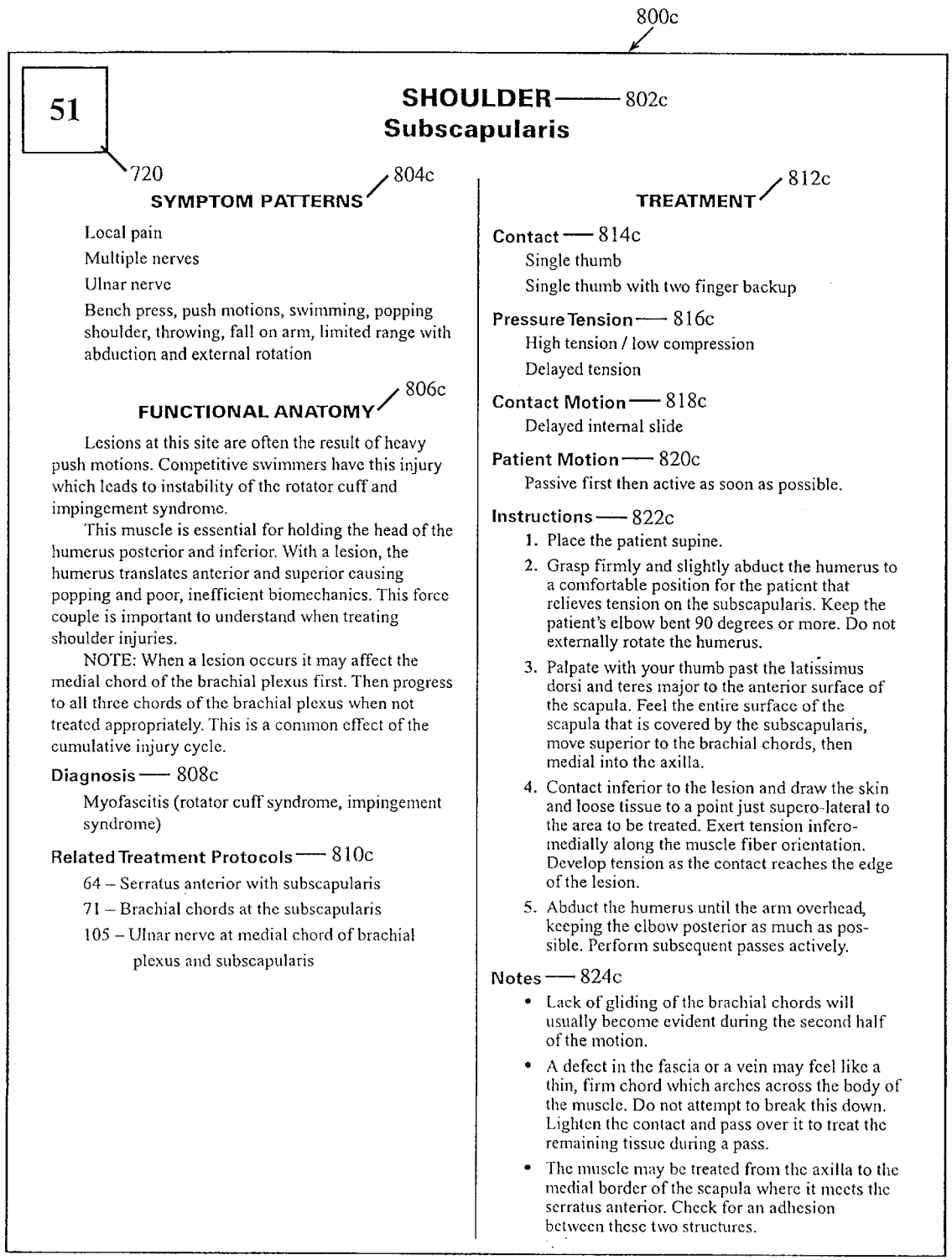

800c

| 51 | SHOULDER ——— 802c |
| | Subscapularis |

720    804c

SYMPTOM PATTERNS

Local pain

Multiple nerves

Ulnar nerve

Bench press, push motions, swimming, popping shoulder, throwing, fall on arm, limited range with abduction and external rotation

FUNCTIONAL ANATOMY 806c

Lesions at this site are often the result of heavy push motions. Competitive swimmers have this injury which leads to instability of the rotator cuff and impingement syndrome.

This muscle is essential for holding the head of the humerus posterior and inferior. With a lesion, the humerus translates anterior and superior causing popping and poor, inefficient biomechanics. This force couple is important to understand when treating shoulder injuries.

NOTE: When a lesion occurs it may affect the medial chord of the brachial plexus first. Then progress to all three chords of the brachial plexus when not treated appropriately. This is a common effect of the cumulative injury cycle.

Diagnosis —— 808c

Myofascitis (rotator cuff syndrome, impingement syndrome)

Related Treatment Protocols —— 810c

64 – Serratus anterior with subscapularis

71 – Brachial chords at the subscapularis

105 – Ulnar nerve at medial chord of brachial plexus and subscapularis

TREATMENT 812c

Contact —— 814c

Single thumb

Single thumb with two finger backup

Pressure Tension —— 816c

High tension / low compression

Delayed tension

Contact Motion —— 818c

Delayed internal slide

Patient Motion —— 820c

Passive first then active as soon as possible.

Instructions —— 822c

1. Place the patient supine.
2. Grasp firmly and slightly abduct the humerus to a comfortable position for the patient that relieves tension on the subscapularis. Keep the patient's elbow bent 90 degrees or more. Do not externally rotate the humerus.
3. Palpate with your thumb past the latissimus dorsi and teres major to the anterior surface of the scapula. Feel the entire surface of the scapula that is covered by the subscapularis, move superior to the brachial chords, then medial into the axilla.
4. Contact inferior to the lesion and draw the skin and loose tissue to a point just supero-lateral to the area to be treated. Exert tension infero-medially along the muscle fiber orientation. Develop tension as the contact reaches the edge of the lesion.
5. Abduct the humerus until the arm overhead, keeping the elbow posterior as much as possible. Perform subsequent passes actively.

Notes —— 824c

- Lack of gliding of the brachial chords will usually become evident during the second half of the motion.
- A defect in the fascia or a vein may feel like a thin, firm chord which arches across the body of the muscle. Do not attempt to break this down. Lighten the contact and pass over it to treat the remaining tissue during a pass.
- The muscle may be treated from the axilla to the medial border of the scapula where it meets the serratus anterior. Check for an adhesion between these two structures.

| 53 | SHOULDER —— 802d |
|---|---|
| | Infraspinatus / Teres Minor with Deltoid |

1704

SYMPTOM PATTERNS /804d

Local pain

Pulling / external rotation motions, difficulty reaching overhead and forward

FUNCTIONAL ANATOMY /806d

During most motions of the shoulder, the infraspinatus and teres minor slide underneath the deltoid. Sometimes an adhesion develops at the lateral edge of the infraspinatus and teres minor, and the inferior edge of the posterior deltoid.

The infraspinatus and teres minor may also be adhered to the deltoid as it passes under it and around the humerus.

Diagnosis —— 808d

Myofascitis

Related Treatment Protocols —— 810d

45 – Deltoid
52 – Infraspinatus
54 – Teres minor

TREATMENT /812d

Contact —— 814d

Single thumb

Pressure Tension —— 816d

Delayed tension

Contact Motion —— 818d

Internal and external slide

Patient Motion —— 820d

Active

Instructions —— 822d

1. Adduct the humerus with the patient prone.
2. Contact the inferior edge of the posterior deltoid and draw tension medially, arriving at the teres minor with your contact as much under the deltoid as possible.
3. Have the patient reach overhead, keeping the thumb pointing to the floor.

Infraspinatus Under Deltoid

1. Forward flex and externally rotate the humerus.
2. Contact the deltoid just anterior to the infraspinatus and traction the deltoid posterior along the fibers of the infraspinatus.
3. Maintain the traction while internally rotating the humerus.

Notes —— 824d

- During patient motion, hold firm tension along the deltoid until it increases abruptly. Then draw your contact medially, trying to work between the muscles while letting the infraspinatus and teres slide underneath.

Figure 18

| 71 | SHOULDER — 802e
Brachial Chords at Subscapularis |

2004

SYMPTOM PATTERNS / 804e

Ulnar nerve

Multiple nerves

Ulnar nerve / medial chord first, all three chords second, whole hand

FUNCTIONAL ANATOMY / 806e

The medial chord of the brachial plexus is usually the first of the chords to be entrapped with the subscapularis. If this process is allowed to worsen, the posterior and lateral chords follow. The brachial chords normally slide in excess of 1.5 centimeters during abduction of the humerus. When an adhesion occurs, it will exert a significant pull on the nerves during this motion.

The chords can be palpated by sliding your contact superior on the subscapularis to the roof of the axilla. The neurovascular sleeve should be palpable on the side of the contact thumb. It is possible to slide your contact to the anterior side of the sleeve and sometimes to the superior side as well. Take care to avoid applying undue compression on the nerves.

During treatment, it is common and desirable to duplicate the exact neurological symptoms. These usually subside in less than a minute, and the patient should be advised. As you palpate the nerve entrapment it is even possible to predict the symptom duplication.

Diagnoses — 808e

Peripheral nerve entrapment

Myofascitis

Related Treatment Protocols — 810e

51 – Subscapularis

90 – Neurovascular sleeve at coraco-pectoral tunnel

91 – Neurovascular sleeve at coracobrachialis

TREATMENT / 812e

Contact — 814e

Single thumb

Pressure Tension — 816e

High tension / low compression

Contact Motion — 818e

Internal and external slide

Patient Motion — 820e

Active

Instructions — 822e

1. Place the patient supine and support the humerus with a firm comfortable grasp. Adduct the humerus to relieve tension on the subscapularis. Flex the elbow 90 degrees or more. Do not externally rotate the humerus. Palpate with your thumb past the latissimus dorsi and teres major to the anterior surface of the scapula, then superior to the brachial chords.

2. Contact inferior to the lesion. Draw the patient's skin and loose tissue to a point between the muscle and nerve. Exert tension along the nerve / muscle junction until sufficient tension is achieved.

3. Abduct the humerus, delaying motion of your contact until tension is felt to develop. Proceed within patient limits until the arm is raised overhead and the elbow is posterior as much as possible.

Notes — 824e

- Try to slide your contact between the muscle and nerve while holding the subscapularis medially and letting the nerve slide laterally. Make the second pass actively.

- Lack of brachial-chord sliding will usually become evident during the second half of the motion.

Figure 21

| 90 | SHOULDER / ARM / HAND —— 802h |
|---|---|
| | Neurovascular Sleeve at Coraco-Pectoral Tunnel |

2004

SYMPTOM PATTERNS  /804h

Multiple nerves

Non nerve root symptoms, odd neurological patterns, all nerves, whole hand, difficult abduction/external rotation

FUNCTIONAL ANATOMY  /806h

The neurovascular sleeve holds the axillary artery, vein, and all the nerves into the upper extremity. This structure slides in excess of 1.5 centimeters through this thoracic outlet. When an adhesion occurs, it will exert a significant pull on the nerves during humeral abduction.

The sleeve may be palpated by sliding your contact superior on the subscapularis to the roof of the axilla. The neurovascular sleeve should be palpable on the side of the contact thumb. It is possible to slide your contact to the anterior side of the sleeve, and sometimes to the superior side of it as well. Avoid applying undue compression on the nerves.

Palpate along the posterior side of the pectoralis minor to the coracoid process at which point the sleeve is palpable. It is usually possible to work your contact between the pectoralis minor and the sleeve. The neurovascular sleeve may sometimes be traced and worked all the way to the clavicle and scalenes at the first rib.

Diagnoses —— 808h

Peripheral nerve entrapment

Myofascitis

Related Treatment Protocols —— 810h

44 – Coracobrachialis

47 – Pectoralis minor

51 – Subscapularis

85 – Neurovascular sleeve at the coracobrachialis

TREATMENT  /812h

Contact —— 814h

Single thumb

Pressure Tension —— 816h

High tension / low compression

Contact Motion —— 818h

Internal and external slide

Patient Motion —— 820h

Active

Instructions —— 822h

1. Orient the patient supine. Slightly abduct the humerus, supporting the patient's upper arm with a firm comfortable grasp. Flex the elbow 90 degrees or more, and do not externally rotate the humerus. Protract the shoulder.

2. Palpate with your thumb along the posterior side of the pectoralis minor to the sleeve and coracoid process. Exert medial tension along the nerve / muscle junction until sufficient tension is achieved.

3. Abduct the humerus, delaying supero-medial contact motion until tension develops. End with over 90 degrees abduction and maximum posterior extention. Stay within patient tolerance.

Notes —— 824h

- Try to slide your contact between the muscle, or coracoid and nerve, while holding the muscle medially and letting the sleeve slide laterally. Follow the neurovascular sleeve as far toward the first rib and scalenes as possible.

- Lack of gliding of the sleeve will usually become evident during the second half of the motion.

Figure 28

| 92 | WRIST / FOREARM — 802i |
|---|---|

Radial Nerve at Distal Brachioradialis

2012

SYMPTOM PATTERNS / 804i

Radial nerve
Local pain
DeQuervain's, tennis elbow, grasp and lift, fast pitch softball

FUNCTIONAL ANATOMY / 806i

The brachioradialis is classified as an elbow flexor, but it is in a poor position to accomplish the task. It is active during a grasp-and-lift motion, especially if the wrist is neutral. It lies along the extensor carpi radialis longus for its entire length, but it does not cross the wrist. It's relationship to the first compartment of the extensor retinaculum, and the fascia around the wrist, is important to entrapment of the superficial branch of the radial nerve.

The extensor carpi radialis muscles can also be involved with the brachioradialis in compromising the superficial branch of the radial nerve. The radial nerve can also be trapped between the brachioradialis and the brachialis.

Diagnoses — 808i

Peripheral nerve entrapment
Myofascitis

Related Treatment Protocols — 810i

13 – Extensor pollicis brevis and abductor pollicis longus
14 – Extensor and abductor pollicis with extensor retinaculum
27 – Pronator teres
30 – Extensor carpi radialis
35 – Brachioradialis
39 – Brachialis

TREATMENT / 812i

Contact — 814i
Single thumb
Double thumb

Pressure Tension — 816i
High tension / low compression

Contact Motion — 818i
Internal and external slide

Patient Motion — 820i
Active or passive

Instructions — 822i
1. Flex the patient's elbow and supinate the wrist.
2. Contact along the muscle and traction proximally.
3. Extend the patient's elbow and draw your contact proximally. At the end of this motion, pronate the wrist.

Notes — 824i
- Working the entire tendon and muscle body requies several passes over multiple areas to reach the humeral attachment next to the brachialis.
- Apply tension and pressure judiciously over the distal attachment. This area is often sensitive and reacts adversely to excessive pressure.

Figure 30

EXPERT SYSTEM SOFT TISSUE ACTIVE MOTION TECHNIQUE FOR RELEASE OF ADHESIONS AND ASSOCIATED APPARATUS FOR FACILITATING SPECIFIC TREATMENT MODALITIES

Microfiche Appendix

A microfiche appendix is submitted with this application 3 fiches and 252 pages. The microfiche appendix includes a listing or database of images showing a preferred embodiment of practicing the present invention. These images depict one-hundred and five non-limiting examples of preferred treatment modalities according to the invention, but do not exhaust all possibilities for treatment modalities. These images also include four pages of symptom pattern diagrams permitting a selection of treatment modalities according to the present invention.

BACKGROUND OF THE INVENTION

1. Field of the Invention

The present invention relates to the field of medical treatments for reducing the size and effect of various adhesions or lesions in soft tissues, such as muscles, tendons, blood vessels, fascia, and nerves. More specifically, medical treatments according to the invention utilize an expert system for directing the non-surgical manual manipulation of soft tissues to identify and treat soft tissue adhesions that cause numbness, pain, and restricted range of motion.

2. Statement of the Problem

Unnecessary surgeries are sometimes performed because the medical profession lacks a unified and comprehensive training program for the non-surgical treatment of all types of soft tissue lesions. Prior treatments and training have focused on specific disorders, which results in an ad hoc overall level of expertise in the medical profession and a preference for surgical intervention. Medical practitioners are often unaware of non-surgical treatments offering higher success rates and less trauma to their patients than can be obtained from surgical procedures. There is a need for an expert system to guide medical doctors, chiropractors, physical therapists, and occupational therapists in implementing protocols for the non-surgical treatment of all types of soft tissue lesions. This expert system would prevent unnecessary surgeries.

Historically, a preferred treatment modality has been the surgical excision of lesions, if possible, once they become problematic. These surgeries may not be needed even though they may be commonplace. By way of example, surgery for carpal tunnel syndrome can be performed to divide the transverse carpal ligament in a manner that relieves pressure on the median nerve. U.S. Pat. No. 5,501,657 to Feero reports that surgical techniques intended to relieve the syndrome have a failure rate ranging from 50% to 75%. The '657 patent teaches a non-surgical technique for the relief of pain associated with carpal tunnel syndrome. The massage technique includes stretching muscles of the forearm and hand combined with longitudinal manipulation of the forearm muscles to improve circulation. Even though the '657 patent does not identify a success rate for the technique that it teaches, the technique is said to be more successful than prior surgical techniques.

Surgical techniques for soft tissue injuries have low success rates because surgery cannot address all of the potential problem areas. Additionally, surgery itself produces trauma. Leahy in *New Treatment of Carpal Tunnel Syndrome,* Chiropractic Sports Medicine (1992) proposed a non-surgical technique for the treatment of carpal tunnel syndrome. Leahy recognized that carpal tunnel syndrome may involve lesions of the carpal canal, the median nerve, the radial nerve, the posterior interosseus nerve, the axilla, the anterior interosseous nerve, and the ulnar nerve. Thus, the blanket designation of 'carpal tunnel syndrome' is inadequate to describe the afflicted anatomy with particularity.

Cumulative Injury Disorders

Cumulative injury disorders involve the soft tissues, and are now perhaps the most significant injury problem in the United States. Federal injury statistics indicate that cumulative injury disorders have worsened by six hundred and seventy percent in the last five years. A variety of injuries including carpal tunnel syndrome may be classified under the broad heading of cumulative trauma disorders or cumulative injury disorders. These disorders include a group of injuries to the muscles, tendons, bones, blood vessels, fascia, and nerves. The term 'cumulative injury disorder' is preferred because actual trauma is not necessarily required to bring about the injury.

The three basic injury types include acute injuries, repetitive motion injuries, and constant pressure or tension injuries. Acute injuries result from the tearing of muscle and fascia, and are most often associated with immediate inflammation. Acute injuries trigger biological processes involving white blood cells, the production of fibrinogen, and the growth of adhesions. Adhesions also result from the other types of injuries.

Cumulative injuries result from the law of repetitive motion and the cumulative injury cycle. The law of repetitive motion may be modeled as:

$$I=NF/AR, \qquad (1)$$

wherein I is a relative quantity denoting an insult to the tissues; N is a number of repetitions; F is the force or tension of each repetition as a percent of maximum muscle strength; A is the amplitude of each repetition; and R is the relaxation time between each repetition. For example, a jackhammer operator is daily exposed to vibrations wherein N is high, A is low, and R is low. Thus, I is high. Formula (1) above shows that injuries may derive from constant pressure or tension that is without apparent or immediate trauma to soft tissues. Furthermore, cumulative injuries may result from isometric muscle contractions and poor posture with consequences including cellular calcium retention, poor cellular repair, and altered function.

The Cumulative Injury Cycle

The three basic injury types may all contribute to a cumulative injury cycle 100, as shown in FIG. 1. Repetitive motion injuries result in weak and tense tissues 102. Tissues that are adjacent to these weak and tense tissues may also be drawn tight. Weak and tense tissues produce corresponding internal forces 104 including friction and pressure. An acute injury 106, such as tearing or crushing on a microscopic or macroscopic level, can result from these internal forces. An isolated acute injury 106 can also commence cycle 100. Inflammation 108 results from the acute injury 106, and exacerbates the total problem by enhancing the weakness and tenseness of the injured tissues. Internal forces 104 also induce decreased circulation or edema 108. The effect of these internal forces is usually a decrease in circulation. The acute injury 106 and inflammation 108 contribute to cellular hypoxia from restricted circulation. This cellular hypoxia causes fibrosis and adhesions 110 to occur in and between tissues. Acute injury 106 and inflammation 108 combine to form an inflammation cycle 112 leading to adhesion and fibrosis 110. A chronic cycle 114 also leads towards adhesion and fibrosis 110. Chronic cycle 114 includes the effects of decreased circulation and edema 116. As indicated above, internal forces 104 lead to a decrease in circulation and an increase in internal pressure. The decrease in circulation may be enhanced by the continued application of external pressure, e.g., as from an elastic garment. Pressure applied over a low-pressure lymphatic channel causes swelling or edema, which also leads to adhesion and fibrosis 110.

Certain persons are predisposed to be more affected than others by injuries on the cumulative injury cycle 100. For example, smokers and diabetics have relatively poor circulation, which helps perpetuate the cycle. Thyroid deficits and hormonal changes increase musculature tension, and enhance the degree of weakness and tightness in the affected tissues.

The cumulative injury cycle 100 perpetuates itself, and afflicted persons find themselves in a downward spiral until the symptoms and syndromes of cumulative injury disorder are prevalent. Examples of cumulative injury disorders include carpal tunnel syndrome, cubital tunnel syndrome, epicondylitis, tenosynovitis, myofascitis, bursitis, peripheral nerve entrapment, thoracic outlet syndrome, De Quervain's disease, and others.

Conventional Treatment Methodology

Conventional training disposes those in the medical profession to a sequential protocol involving the treatment of patients, namely, history, evaluation, diagnosis and then treatment. The patient's history is taken to determine what symptoms the patient has experienced and for how long, what treatments have been applied, and what has been the effect of those treatments. In the evaluation stage, the patient may be subjected to testing that confirms symptoms or conditions that are to be expected in conjunction with respective diagnostic options. A diagnosis is made based upon the results of the history and evaluation stages. Only then is there adopted a treatment modality addressing the diagnosed problem.

The conventional approach is problematic in the diagnosis and treatment of soft tissue disorders because the evaluation is often flawed due to the ad hoc level of expertise in the medical profession. The physician selects a particular treatment based upon this diagnosis; however, the treatment may be flawed because it neglects some of the affected areas. The physician may also be bombarded with conflicting or incomplete reports of existing treatment modalities. For example, stretching and bending of the forearm according to Feero in U.S. Pat. No. 5,501,657 does not affect all of the nerves noted by Leahy. In another example, a physical examination or evaluation designed to detect carpal tunnel syndrome may lead to a diagnosis of carpal tunnel syndrome because a physician expects to see this disorder and has conducted the physical examination to confirm it. Surgery may subsequently be performed to relieve pressure on the median nerve, but symptoms of carpal tunnel syndrome may occur even when the median nerve is not compressed at the carpal tunnel.

There remains a true need for an expert system in diagnosing and treating soft tissue lesions. The expert system would avoid misdiagnosis and provide non-surgical treatment modalities having a greater chance of success than that which surgical techniques offer.

SOLUTION

The present invention overcomes the aforementioned problems by providing an expert system for diagnosing and treating soft tissue lesions. Clinical experience has shown that the success rate in treating soft tissue adhesions according to the non-surgical protocols set forth below is approximately ninety four percent. This phenomenal success rate far exceeds that which is obtainable from surgical methods and exists, in part, because the expert system works in a non-traditional manner permitting health care providers to implement a treatment that combines diagnosis and evaluation. The expert system avoids the traditional need for diagnosis and evaluation prior to beginning treatment by mapping visual images of symptom patterns to specially designed treatment protocols. This new method of beginning treatment prior to diagnosis and evaluation is very different from prior treatment methods, which follow the sequential steps of history, evaluation, diagnosis, and then treatment.

The broadest concept of the invention includes an expert system for medical practitioners to use in the non-surgical treatment of soft tissue lesions. The medical practitioner and a patient study a plurality of indicia representing symptom pattern images or charts. Each symptom pattern image provides an association between an anatomical image showing a portion of the human body and an expert-derived symptom pattern that is superposed on the anatomical image. The expert-derived symptom pattern depicts an anatomical area where a medical expert has determined that soft tissue lesions produce symptoms, such as numbness, tingling, pain, ache, burning, weakness, atrophy, circulatory changes, hypersensitivity, restricted motion, and combinations of these symptoms. An identifier is used to associate each of the respective symptom pattern images with one or more corresponding expert treatment protocols. Both the symptom pattern images and the treatment protocols include a cross-reference list of related treatment protocols. This cross-reference list is useful because very different soft tissue lesions may produce similar or identical symptoms. Thus, an effective treatment may be implemented from a battery of diagrams without a confirmed diagnosis ever having been made.

The expert system avoids problems that are inherent to traditional medical treatment methods because it permits treatment to begin even before the medical practitioner has made a diagnosis or completed an evaluation. A patient is interviewed to identify the anatomical area or areas on his or her person where the patient is experiencing the symptoms from the list of symptoms identified above, e.g., numbness or tingling sensations. This anatomical area is referred to herein as the patient's symptom pattern. The locus of the patient's symptom pattern is matched with a selected symptom pattern image. The selected symptom pattern image is selected from a plurality of such images, which may be displayed to the patient from a book, computer database, or wall chart. Thus, matching of the patient's symptom pattern with a symptom pattern image preferably occurs by asking the patient to select a symptom pattern chart that shows an expert-derived symptom pattern corresponding to the locus of the patients symptoms. The medical practitioner who implements the treatment may assist the patient's selection of an appropriate symptom pattern chart by suggesting selected symptom pattern charts and recalling them from storage to present them for the patient's review.

The selected symptom pattern chart is preferably associated by an identifier with one or more expert treatment protocols. For example, this identifier can be the number of a corresponding expert treatment protocol, and the number can be found as indicia on the symptom pattern chart. The expert treatment protocol is used to diagnose and treat a soft tissue lesion in the patient. If the selected treatment fails to reproduce the symptoms that the patient has been experiencing or the medical practitioner cannot feel the adhesion in the correct spot, then another treatment protocol may be selected and implemented from the cross-reference list of related treatment protocols. The shared identifier is used to match the symptom pattern image with an a corresponding treatment protocol for appropriate recall on demand whether the symptom pattern images are found in a book, computer image database, or chart.

As indicated above, the treatment protocols include specific techniques for manually manipulating the patient's body to effect treatment of the patient's soft tissue lesions. This manual manipulation occurs proximate the locus of the expert-derived symptom pattern and the patient's symptom pattern as directed by the expert treatment protocol. It is essential to the high success rate of the expert system treatment that the manual manipulation of the patient's body include moving the patient's symptom pattern area while holding a portion of the patient's anatomy including the patient's symptom pattern area in tension at a contact point. This movement under tension causes soft tissues underlying the contact point to pass longitudinally beneath the contact point with respect to fibers in the tissues. This movement is preferably done actively by the patient, but may also be done passively by the medical practitioner if the patient is incapable or does not want to perform the motion. The expert treatment protocols facilitate this manipulation by providing an anatomical diagram showing the location of subcutaneous tissues involved in active motion.

Use of the expert system permits medical practitioners to implement treatment before they have conducted an evaluation and diagnosis. The medical practitioner confirms an expert diagnosis found in the expert treatment protocol by feeling for the presence of a soft tissue lesion during the prescribed treatment. The diagnosis is further confirmed if he or she can reproduce the soft tissue adhesion symptoms during treatment. Thus, the treatment can be selected and its application can be started without the medical practitioner ever having to perform an evaluation and diagnosis; the treatment becomes the evaluation. This aspect of using the expert system avoids misdiagnosis with the associated consequence of improperly administered treatments.

Apparatus for use in connection with this treatment includes means for storing the symptom pattern charts and for associating each of the charts with one or more corresponding expert treatment protocols. This associating means preferably includes an identifier, e.g., a number, that is shared between the respective symptom pattern charts their corresponding expert treatment protocols. This apparatus can be in the form of a computer database that performs or assists in the function of displaying a selected treatment protocol for use, or it can be in the form of a book including cross indexed symptom pattern charts and treatment protocols.

The apparatus is especially useful as an aid in training others to treat patients according to the claimed invention. Medical practitioners can learn to use method and apparatus according to the invention in seminars or classes where actual or simulated patients are treated or through the use of visual displays, e.g., overhead transparencies, computer displays, or audio visual presentations, showing pictures of actual or simulated treatment in progress.

These and other features, objects, and advantages of the present invention will become apparent to those skilled in the art upon a reading of the detailed discussion below, in combination with the associated drawings.

BRIEF DESCRIPTION OF THE DRAWINGS

FIG. 3A is a sectional view taken across line 3'—3' of FIG. 3;

FIG. 15 depicts an expert treatment protocol for use in treating adhesions of the palmar fascia with symptoms corresponding to another selected one of the symptom pattern images of FIG. 7;

FIG. 18 depicts a treatment protocol for use in the FIG. 6 process according to the FIG. 17 symptom pattern images;

FIG. 21 depicts a treatment protocol for use in the FIG. 6 process corresponding to the FIG. 20 symptom pattern images;

FIG. 28 depicts yet another treatment protocol for use in the FIG. 6 process corresponding to the FIG. 20 symptom pattern images;

FIG. 30 depicts yet another treatment protocol for use in the FIG. 6 process corresponding to the FIG. 20 symptom pattern images;

DETAILED DESCRIPTION OF THE PREFERRED EMBODIMENT

Introductory Principles of Longitudinal Manipulation of Soft Tissues

The expert system of the present invention is designed to provide non-surgical treatments for soft tissue lesions or adhesions. Thus, the treatment can eliminate or reduce the size of soft tissue adhesions that cause symptoms including numbness, tingling, pain, ache, burning, weakness, atrophy, circulatory changes, hypersensitivity, and restricted motion. The treatment also alleviates or eliminates these symptoms.

A key principle of the invention is that soft tissue adhesions can be treated by longitudinal manipulation of soft tissues in cooperation with active or passive motion of the patient's body. Active patient motion is most preferred. It is most desirable to implement treatment by manually contacting the exterior skin of a patient at a contact point that is selected to place subcutaneous tissues of a patient in tension. The subcutaneous tissues include muscles, nerves, ligaments, or tendons. The patient is then moved or moves to slide the subcutaneous tissues longitudinally beneath the contact point. This technique is distinct from traditional massage techniques, which typically do not require patient motion and also move laterally, as opposed to longitudinally, across the respective muscles, nerves, ligaments, or tendons. Thus, the techniques described herein are referred to as manipulation, not massage. The working examples set forth below provide numerous implementations of this soft tissue manipulation technique including longitudinal sliding motion under tension beneath a contact point.

Figure 1:
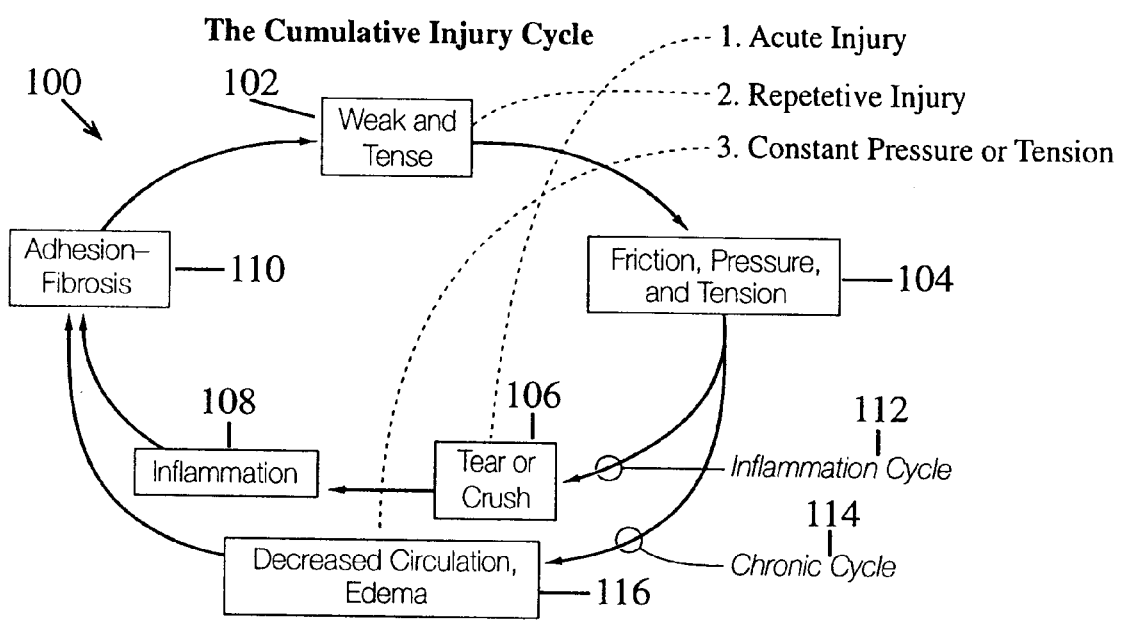
FIG. 1 depicts a diagram of a cumulative injury cycle that is known in the prior art.
Figure 2:
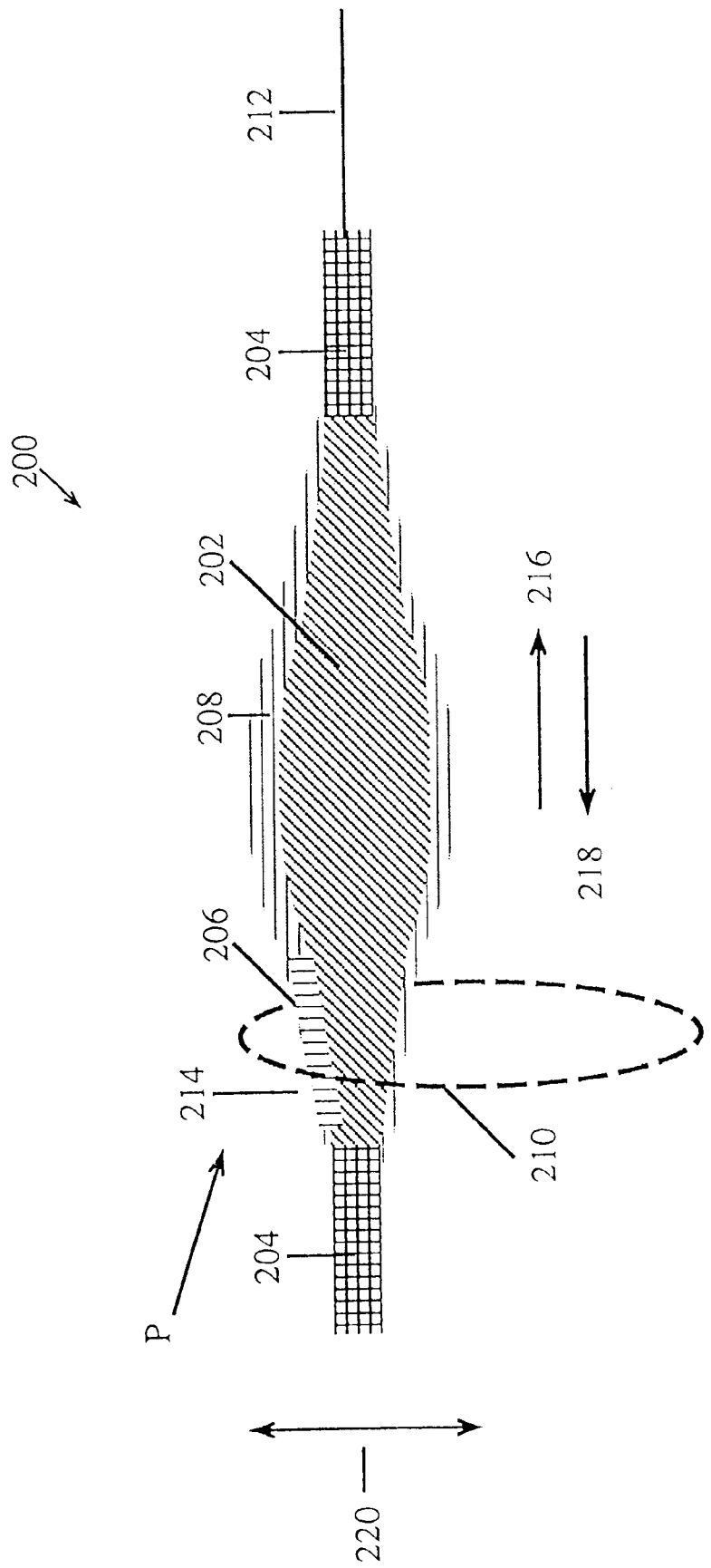
FIG. 2 depicts soft tissue manipulation techniques of the present invention in action on an extensor carpi ulnaris for the treatment of a soft tissue adhesion.

FIG. 2 demonstrates these principles of soft tissue manipulation in action on an extensor carpi ulnaris 200, which includes muscles 202 and tendons 204 located beneath the skin on the posterior portion of the wrist. A normal extensor carpi ulnaris 200 is normally used to extend the wrist, but in this case motion is restricted because a cumulative injury disorder has caused the growth of an adhesion 206 binding extensor carpi ulnaris 200 with synovial sheath 208 and extensor retinaculum 210. Extensor carpi ulnaris 200 presents a longitudinal axis 212. Contractions of muscles in extensor carpi ulnaris 200 naturally cause a shortening of extensor carpi ulnaris 200 along longitudinal axis 212. The interior structure of extensor carpi ulnaris 200 includes a plurality of fibers (not depicted) each having a substantially parallel orientation with respect to longitudinal axis 212. A medical practitioner is exerting external pressure P at contact point 214 on the posterior surface of the wrist.

The patient is asked to raise his or her wrist and fingers. The patient, accordingly, contracts muscles 202 to shorten extensor carpi ulnaris 200. Similarly, the patient is asked to lower his or her little finger and responsively contracts other muscles causing adhesion 214 to slide in longitudinal motion beneath contact point 214 in the direction of arrow 218. In this second motion, the extensor carpi ulnaris 200 is placed in tension by the pressure P at contact point 206. The medical practitioner may passively provide this motion if the patient is unable to do so, but it is preferred for that the patient provide active or voluntary motion whenever possible.

The above discussion referencing FIG. 2 describes what should be done during soft tissue manipulation techniques according to the present invention. In a preferred sense, it is also important that other manipulations not be performed. It is most preferred that the soft tissue manipulation techniques are conducted essentially without lateral motion across the longitudinal axis 212, i.e., avoiding manipulation in the directions of double-headed arrow 220. Furthermore, it is preferred to maintain steady pressure P at contact point 214 and let the patient do essentially all of the movement. Thus, it is preferred that the medical practitioner remain still while exerting pressure P so as not to perform longitudinal sliding motion along longitudinal axis 212. The medical practitioner may also slide contact point 214 along axis 212, but it is necessary, in a preferred sense, that this sliding motion be conducted in a direction that is essentially parallel to axis 212.

Figure 4:
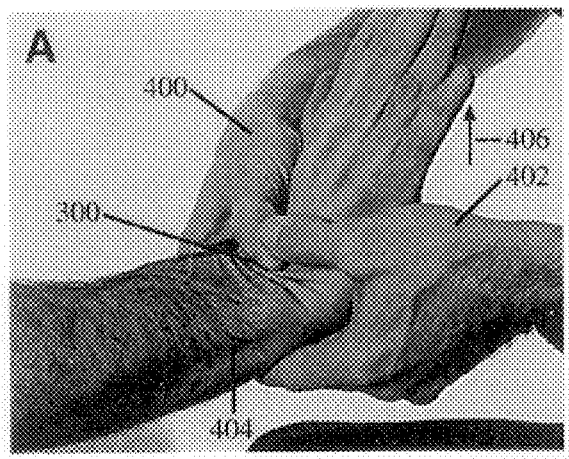
FIG. 4 depicts a photograph of a patient's wrist undergoing treatment of adhesions in the area shown in the anatomical diagram of FIG. 3.
Figure 5:
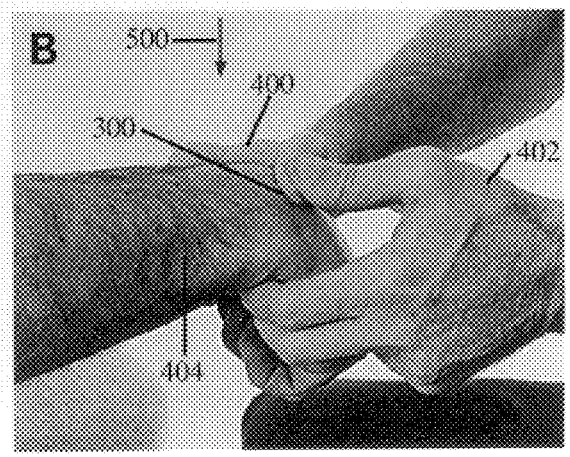
FIG. 5 depicts a photograph of a patient's wrist undergoing additional treatment of adhesions in the area shown in the anatomical diagram of FIG. 3.
Figure 3:
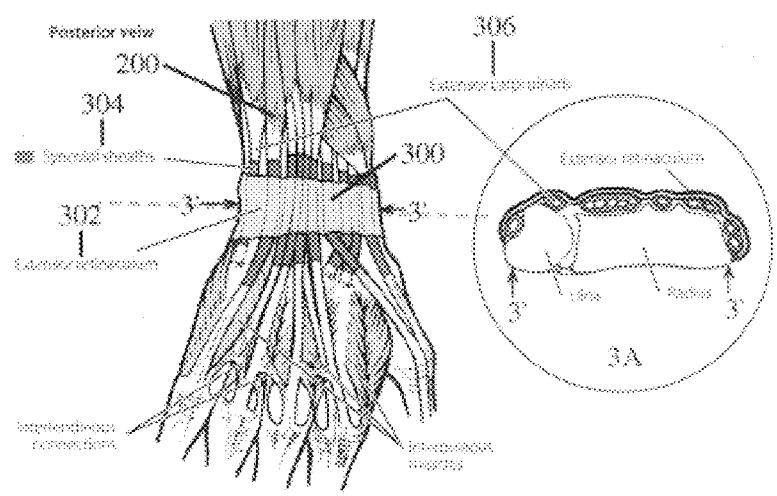
FIG. 3 depicts an anatomical diagram showing a posterior view of the extensor carpi ulnaris and other soft tissues of the wrist.

FIGS. 3–5 depict an example of the soft tissue manipulation techniques of the present invention. FIG. 3 is an anatomical diagram of the subcutaneous tissues of the wrist including extensor tendons with retinaculum. A contact point or contact area 300 exists across the posterior wrist over the extensor retinaculum, synovial sheaths, and extensor carpi ulnaris, which are identified by corresponding indicia 302, 304, and 306. Extensor carpi ulnaris 200 (see also FIG. 2) is shown operably attached in relationship to other anatomical features.

In FIG. 4, the hands 400, 402 of a medical practitioner implementing treatment are placed over contact point 300 of a patient's wrist 404. The patient has actively moved his wrist in an upward direction to provide sliding longitudinal motion beneath contact point 300 in the underlying extensor retinaculum, synovial sheaths, and extensor carpi ulnaris. This motion tensions the portions of the patient's extensor retinaculum, synovial sheaths, and extensor carpi ulnaris, between the patient's elbow and contact point 300. Similarly, FIG. 5 depicts the patient;'s wrist after downward motion in the direction of arrow 500. This downward motion tensions the portions of the patient's extensor retinaculum, synovial sheaths, and extensor carpi ulnaris, between the patient's fingers and contact point 300.

In a typical treatment session, the up and down motions of FIGS. 4 and 5 are repeated from three to eight times to induce corresponding longitudinal sliding motion in the subcutaneous tissues. Analogous contact points for the inducement of similar longitudinal sliding motions exist for virtually every soft tissue in the human or animal body. Repetitions are adjusted as needed to assure patient comfort, and are stopped when the patient experiences undue discomfort or pain. Nevertheless, it is to be expected that the patient will experience a small amount of discomfort when undergoing these repetitions.

Overview of the Treatment Process

Figure 6:
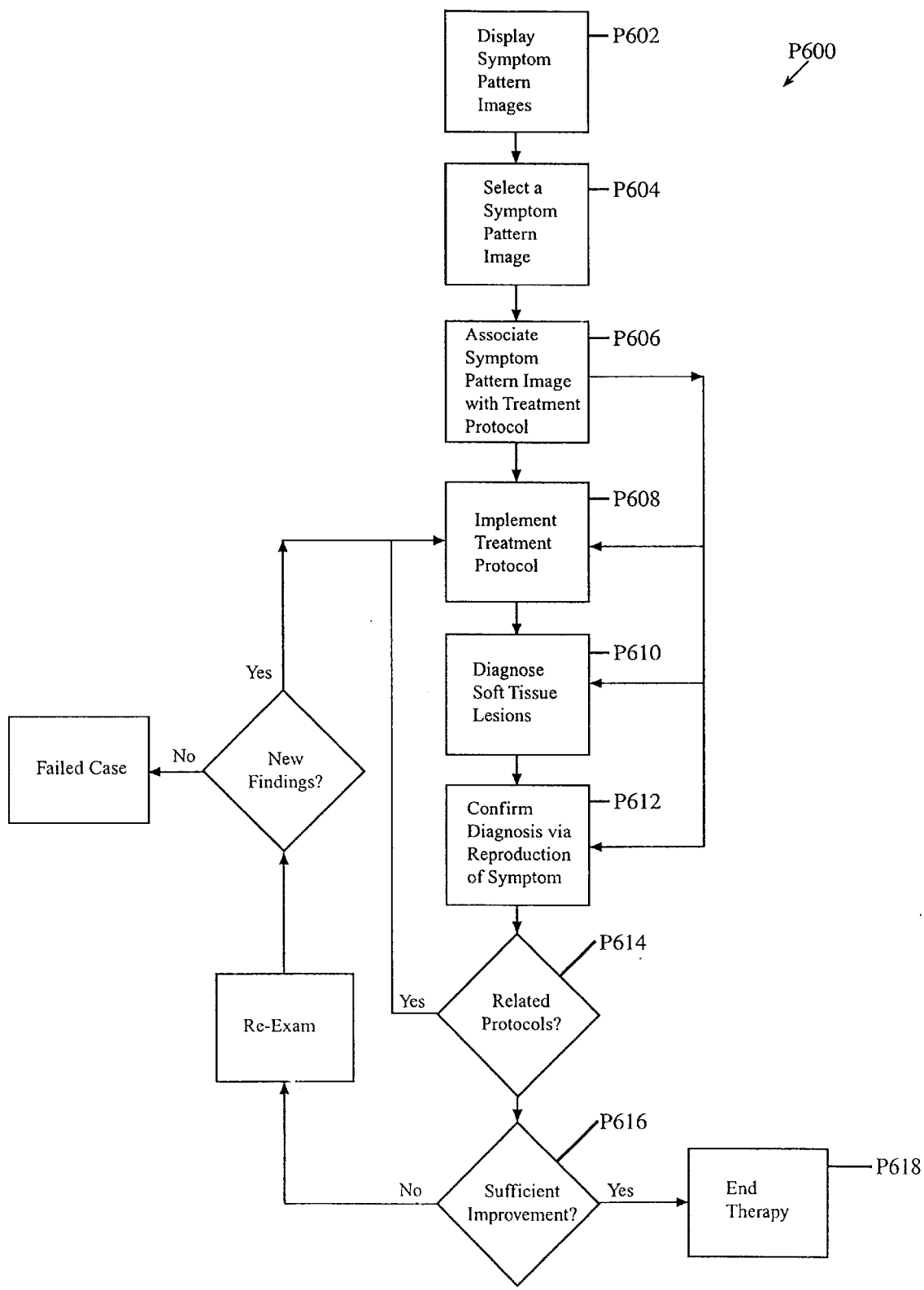
FIG. 6 depicts a schematic process diagram showing a method of non-surgical treatment for soft tissue adhesions according to the present invention.

FIG. 6 depicts a generalized diagram of process P600 for use in treating patients according to the present invention. A significant advantage of process P600 is that it does not require surgery. Soft tissues are manipulated from outside the body to provide therapeutic benefit. Depending upon the needs of individual patients, process P600 can also be used in combination with surgery; however, the surgery falls outside the scope of and is considered distinct from the present invention.

Figure 7:
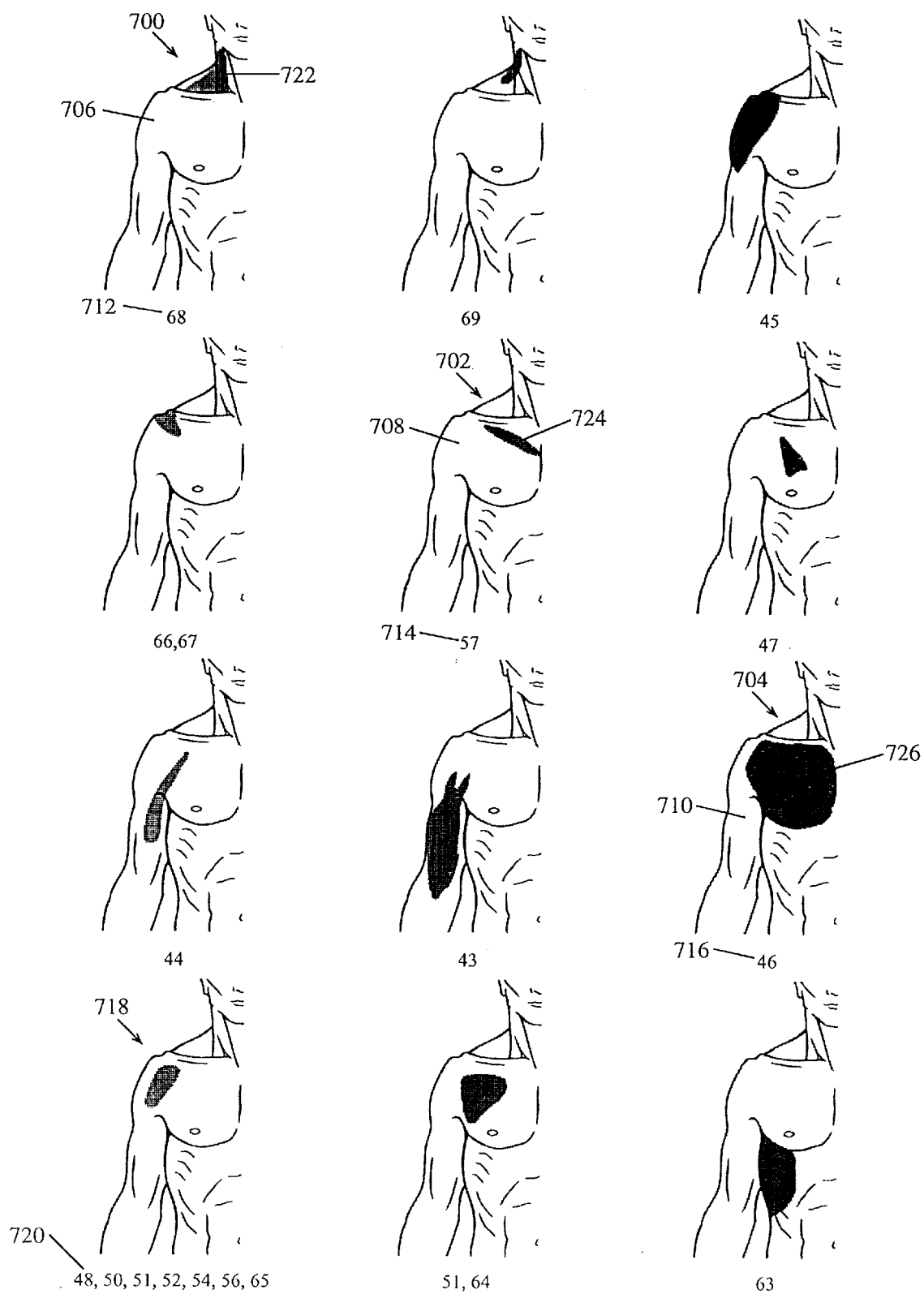
FIG. 7 depicts a plurality of symptom pattern images of the torso and right arm for use in the FIG. 6 process.

Step P602 includes displaying a plurality of symptom pattern images, such as symptom pattern images 700, 702, and 704 shown in FIG. 7. These symptom pattern images and other symptom pattern images are displayed to a patient in need of treatment. At the same time as the symptom pattern images are being displayed to the patient, they are also preferably displayed to a practitioner who will implement treatment. Thus, the medical practitioner can suggest appropriate symptom pattern images to the patient. Suitable means for displaying these images include a book, photographic slide projector or, preferably, a computerized image storage and retrieval system driven by conventional object-oriented code.

In FIG. 7, each symptom pattern image 700, 702, and 704 includes a corresponding anatomical base image 706, 708, or 710, depicting an exterior view of the anterior shoulder in a male patient. An identifier 712, 714, or 716 is associated with each symptom pattern image. The identifier functions as a means for associating a selected symptom pattern image with a corresponding treatment protocol (not depicted in FIG. 7). As in the case of symptom pattern image 718, a single symptom pattern image may be associated with a plurality of identifiers corresponding to a plurality of treatment protocols in a relationship comprising one image to many protocols. A darkened area representing a corresponding expert-derived symptom pattern 722, 724, or 726, is superposed on each anatomical base image. The respective expert-derived symptom patterns 722, 724, and 726, each cover different localized anatomical areas with respect to the underlying base anatomical image. For example, expert-derived symptom pattern 722 is located on the neck of anatomical image 700, while symptom pattern 726 is located on the chest of anatomical image 704. Similarly, expert-derived symptom pattern 724 occupies a smaller area than does expert-derived symptom pattern 726.

The locations of the expert-derived symptom patterns 722, 724, and 726 are selected by medical practitioners who have extensive experience in diagnosing and treating soft tissue lesions or adhesions. The symptom patterns identify the respective locations of symptoms including numbness, tingling, pain, ache, burning, weakness, atrophy, circulatory changes, hypersensitivity, restricted motion, and combinations of these symptoms, which are associated with specific types of soft tissue lesions. Expert medical practitioners who are qualified to identify the location of these symptom patterns include medical doctors, chiropractors, and others who are involved in treating soft tissue lesions.

Returning now to FIG. 6, step P604 includes selecting a symptom pattern image having an expert-derived symptom pattern that most closely covers or resembles the areal extent of symptoms that the patient is experiencing. Ultimately, the patient has to decide which symptom pattern image best corresponds to his or her symptoms. It is recommended that the medical practitioner who intends to implement treatment suggest various symptom pattern images for the patient to review, in order to facilitate the patient making the best selection.

Step P606 includes associating the symptom pattern image with a corresponding treatment protocol. This association is made by use of the identifiers 712, 714, 716, and 720 (see FIG. 7), which correspond to the selected symptom pattern image. For example, symptom pattern image 700 is associated with an identifier indicia 712 comprising the number '68.'

Figure 8:
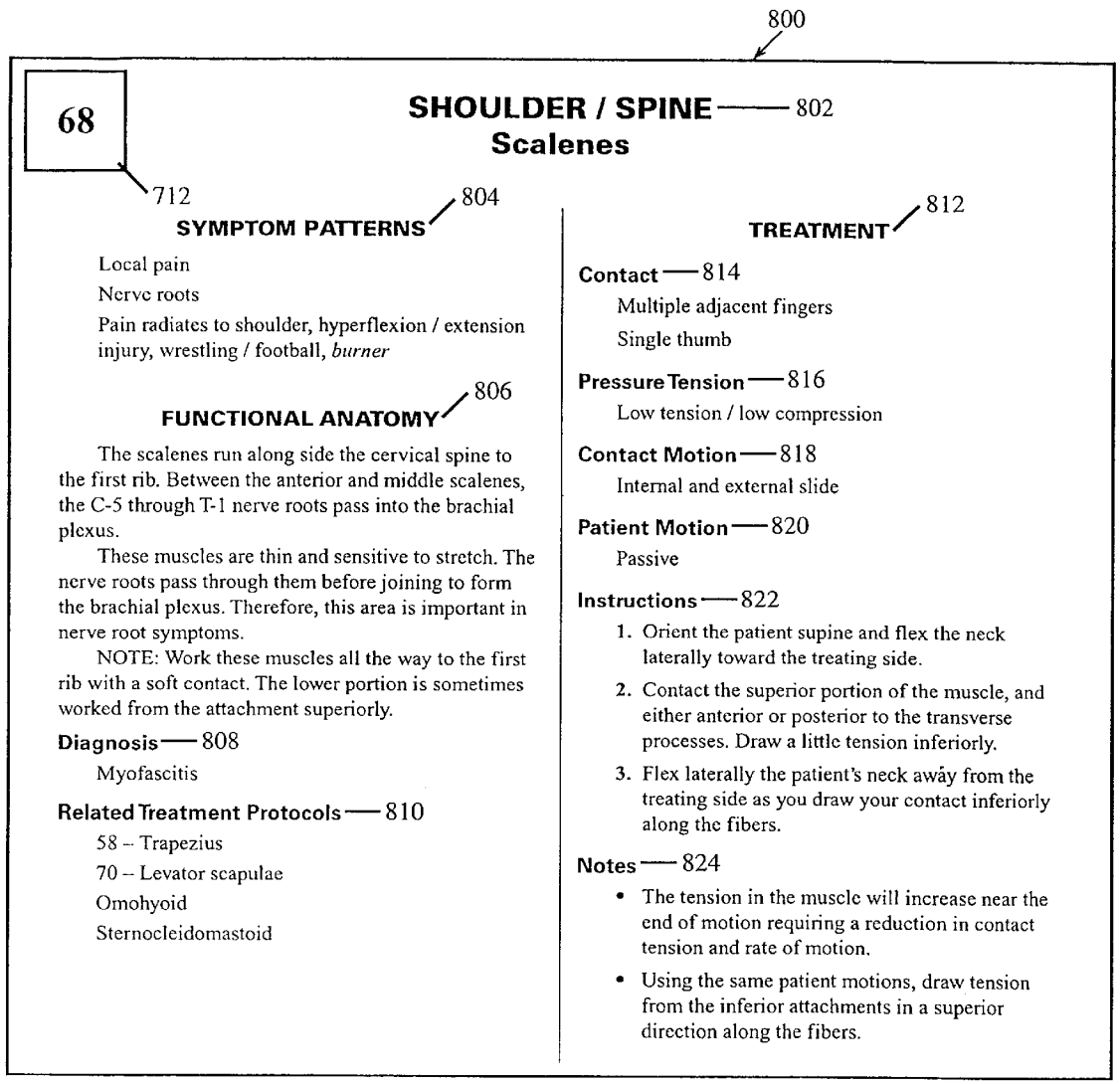
FIG. 8 depicts a treatment protocol for use in the FIG. 6 process according to the FIG. 7 symptom pattern images.

FIG. 8 depicts a treatment protocol 800, which is associated with symptom pattern image 700 of FIG. 7 because it shares the identifier 712 comprising the number '68.' As shown in FIG. 8, treatment protocol 800 includes everything that a skilled medical practitioner requires to implement treatment for soft tissue lesions in the scalenes, according to the longitudinal soft tissue manipulation principles described in FIGS. 2–5. Treatment protocol 800 includes a title 802 providing a general location of the anatomical area where treatment is to be implemented, and a Symptom Patterns section 804 describing the nature of the symptoms involved. Where the symptom pattern image is associated with many identifiers, it is recommended that the medical practitioner read the Symptom pattern section 804 before implementing treatment. It is possible that one or more treatment protocols may be eliminated if the Symptom Pattern 804 description does not correspond to the patient's symptoms.

Treatment protocol 800 also includes a Functional Anatomy section 806 describing in greater detail the anatomical location of the soft tissues where treatment is to be implemented, suggested methods for working or manipulating the anatomical location, a diagnosis 808 corresponding to the selected symptom pattern image 700, and a cross-reference list 810 of related treatment protocols. Treatment protocol 800 also includes Treatment section 812, which provides additional detail with respect to how treatment should be implemented. Subsections of Treatment section 812 include a Contact subsection 814 describing the parts of the provider's hand used to contact the patient. A Pressure Tension subsection 816 provides a relative index of how much pressure and tension are required to effect treatment at the contact point. A Contact Motion subsection 818 describes what type of internal and external motion should be associated with manipulation of the patient at the contact point. A Patient Motion subsection 820 describes whether the patient should move actively or passively. An Instructions subsection 822 provides details of how the medical practitioner should manipulate the patient. A Notes subsection 824 provides special comments and considerations to assure that treatment is being properly implemented.

Figure 9:
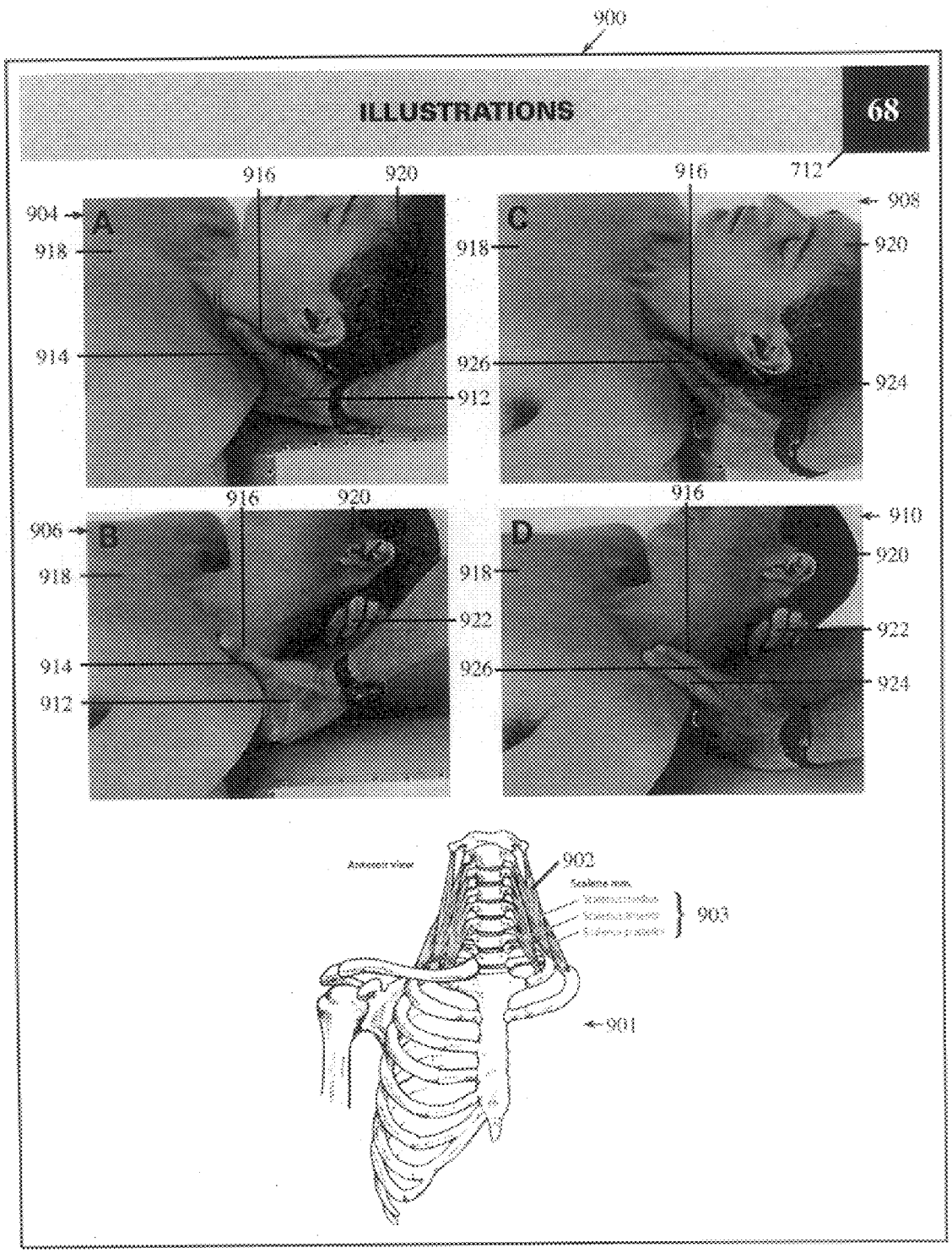
FIG. 9 depicts preferred features of the FIG. 8 treatment protocol.

FIG. 9 depicts additional preferred aspects of treatment protocol 800 including sequentially accessed illustrations 900 of the treatment protocol 800 being implemented on an actual patient. These illustrations 900 include anatomical diagram 901 which, in the case of treatment protocol 800 corresponding to identifier 712 depicts an anterior view of the scalenes 902 annotated with informational indicia 903. Furthermore, a series of photographs 904, 906, 908, and 910, depict the implementation of treatment subsection 812 (see FIG. 8). Photograph 904 shows the left hand 912 of a medical practitioner with the thumb 916 exerting low tension and low compression over contact point 916 on patient 918. Photograph 906 shows the head 920 of patient 918 being passively moved towards the right hand side of patient 918 by the action of the medical practitioner's right hand 922. This motion of head 920 internally slides the scalenes 903 in longitudinal tensile motion beneath contact point 916.

Photographs 908 and 910 show an alternative treatment modality in which the medical practitioner's middle finger 924 and index finger 926 are placed on contact point 916 to effect a treatment that is, otherwise, substantially identical to that shown in photographs 904 and 906. The provision of anatomical diagram 902 together with photographs 904–910 improves treatment by providing the medical practitioner who implements treatment with a better understanding of the longitudinal orientation of the muscle groups being treated. Thus, the medical practitioner is better able to select a contact point 916 to suit the anatomy of a given patient.

Returning now to FIG. 6, step P608 includes consulting the selected treatment protocol (e.g., protocol 800) and manipulating soft tissues of the patient to implement treatment in accord with the selected treatment protocol. Simultaneously with implementation of the treatment protocol, in step P610, the medical practitioner feels for altered tension, texture and movement that constitute soft tissue lesions in the symptom pattern area being treated beneath the contact point. The medical practitioner makes the diagnosis by actually feeling the adhesion. This diagnosis should correspond to the expert diagnosis mentioned in the treatment protocol, e.g., diagnosis 808 of FIG. 8. It is not necessary that there be actual correspondence or confirmation of the expert diagnosis; however, it is recommended to seek other available treatment protocols if the lesion cannot be confirmed where expected by feel, especially if alleviation of the patient's symptoms does not progress.

In step P612, the medical practitioner confirms the diagnosis by interviewing the patient to determine whether the selected treatment protocol has reproduced the symptoms of numbness, tingling, pain, ache, burning, weakness, atrophy, circulatory changes, hypersensitivity, or restricted motion, that the patient has been experiencing. The treatment should reproduce some or all of these symptoms.

Step P614 includes the use of related treatment protocols. It is often advisable for the medical practitioner to further treatment by the additional use of related treatment protocols, such as those mentioned in the Related Treatment Protocol section 810 of FIG. 8. These separate protocols are optionally implemented by a repetition of steps P608–P612 using the new modalities that are associated with each new protocol. The use of additional treatment protocols is strongly recommended when the medical practitioner has been unable, even after treatment, to make a diagnosis because the medical practitioner has been unable to feel a soft tissue lesion or adhesion. Other circumstances where it is recommended to consult additional treatment protocols include instances where the treatment has failed to reproduce symptoms of numbness, tingling, pain, ache, burning, weakness, atrophy, circulatory changes, hypersensitivity, or restricted motion in the patient.

Step P616 includes repeating treatment of the patient at successive time intervals. These time intervals are preferably two or more days apart. Noticeable improvement is often apparent after the very first treatment session. Treatments are concluded at step P618 when, in the judgment of the medical practitioner and the patient, the patients symptoms have improved sufficiently to justify cessation of treatment. Treatments are most preferably stopped when the patient is experiencing no more symptoms, and the medical practitioner can no longer feel the soft tissue lesion or adhesion.

Working Examples

The following non-limiting examples set forth preferred materials and methods for use in practicing the present invention. These examples are representative portions of a larger database of treatment modalities found in the accompanying Microfiche Appendix, which provides a comprehensive program for soft tissues of the upper extremity. These working examples show numerous applications of the principles of soft tissue manipulation seeking therapeutic benefit from longitudinal sliding motions under tension beneath as contact point, as described above with respect to FIGS. 2–5.

EXAMPLE 1

TREATMENT OF THE HAND

ADHESIONS IN THE PALMAR FASCIA

Figure 10:
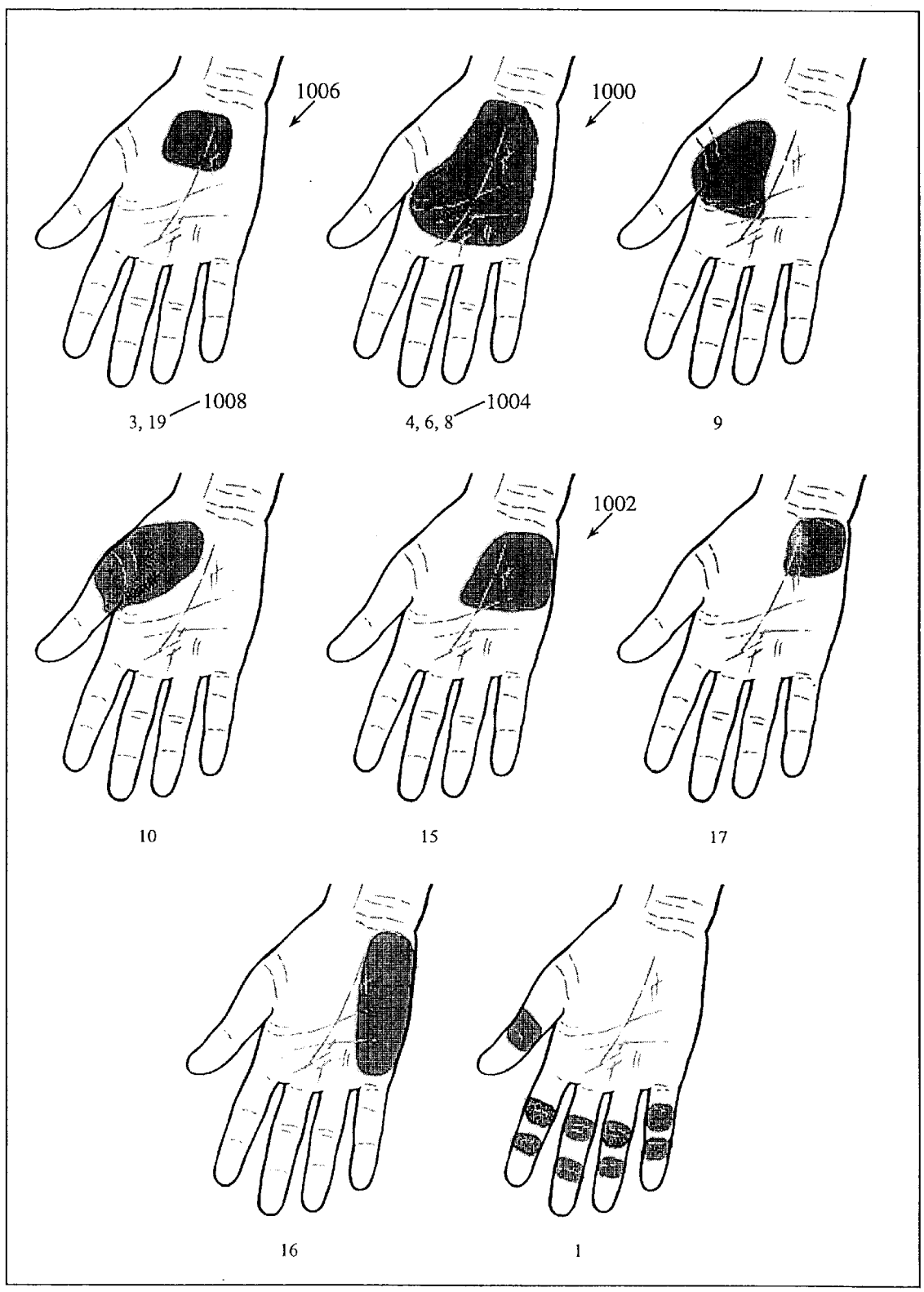
FIG. 10 depicts a plurality of symptom pattern images involving the hand for use according to the FIG. 6 process.

Adhesions of the palmar fascia can cause contractures, such as those which result from Dupuytren's contracture (a fibrosis of the palmar fascia). FIG. 10 depicts a plurality of symptom pattern images, e.g., images 1000 and 1002, including darkened areas comprising expert-derived symptom patterns superposed on base anatomical images of the anterior hand. These symptom pattern images and others are displayed to a patient who complains about a restricted range of hand motion. A patient having Dupuytren's contracture would most likely select symptom pattern image 1000, which includes indicia 1004 associating symptom pattern image 1000 with treatment protocols '4, 6 and 8.'

Figure 11:
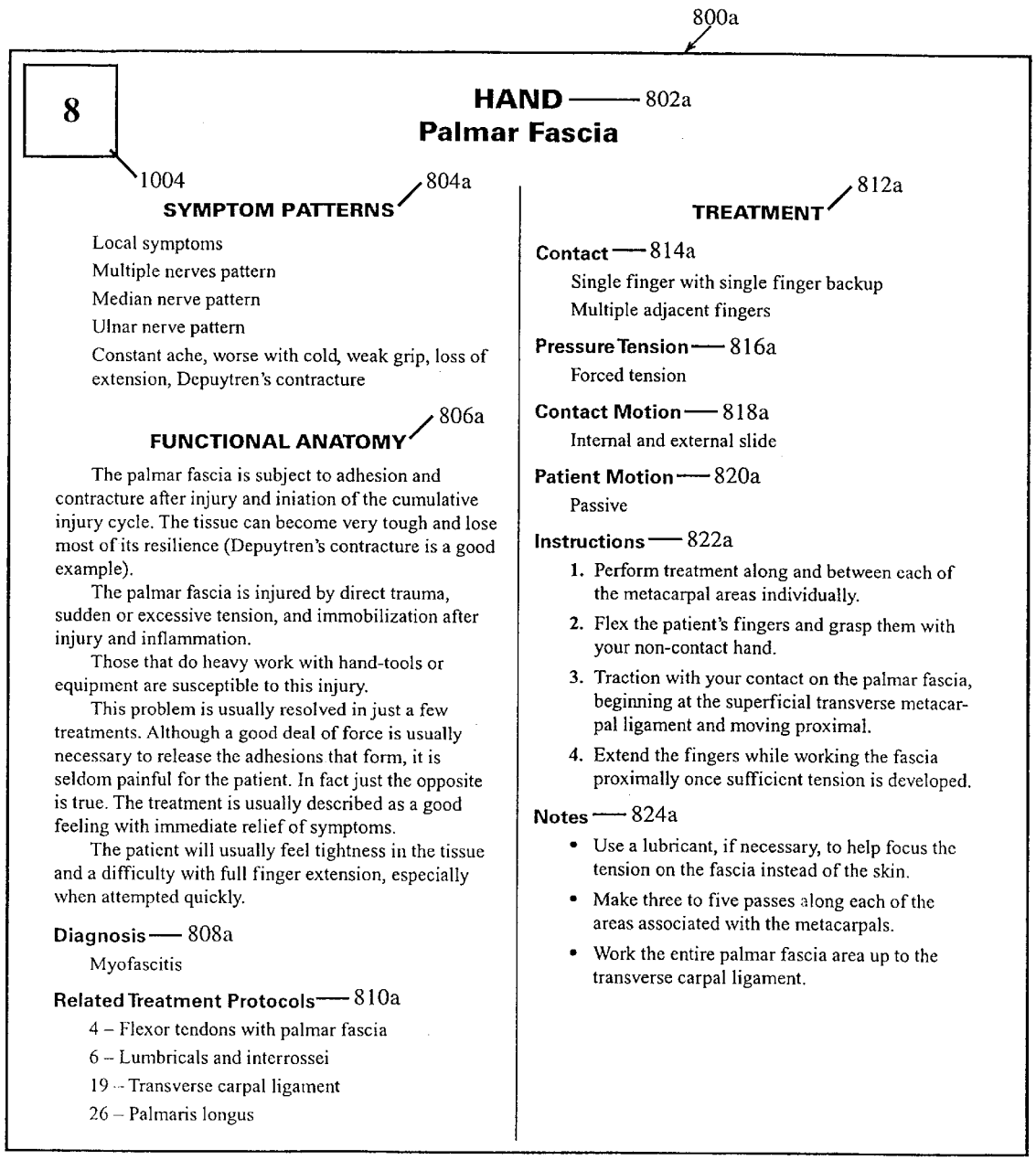
FIG. 11 depicts a sample of a first half of a treatment protocol for use in treating adhesions of the palmar fascia with symptoms corresponding to a selected one of the symptom pattern images shown in FIG. 10.
Figure 12:
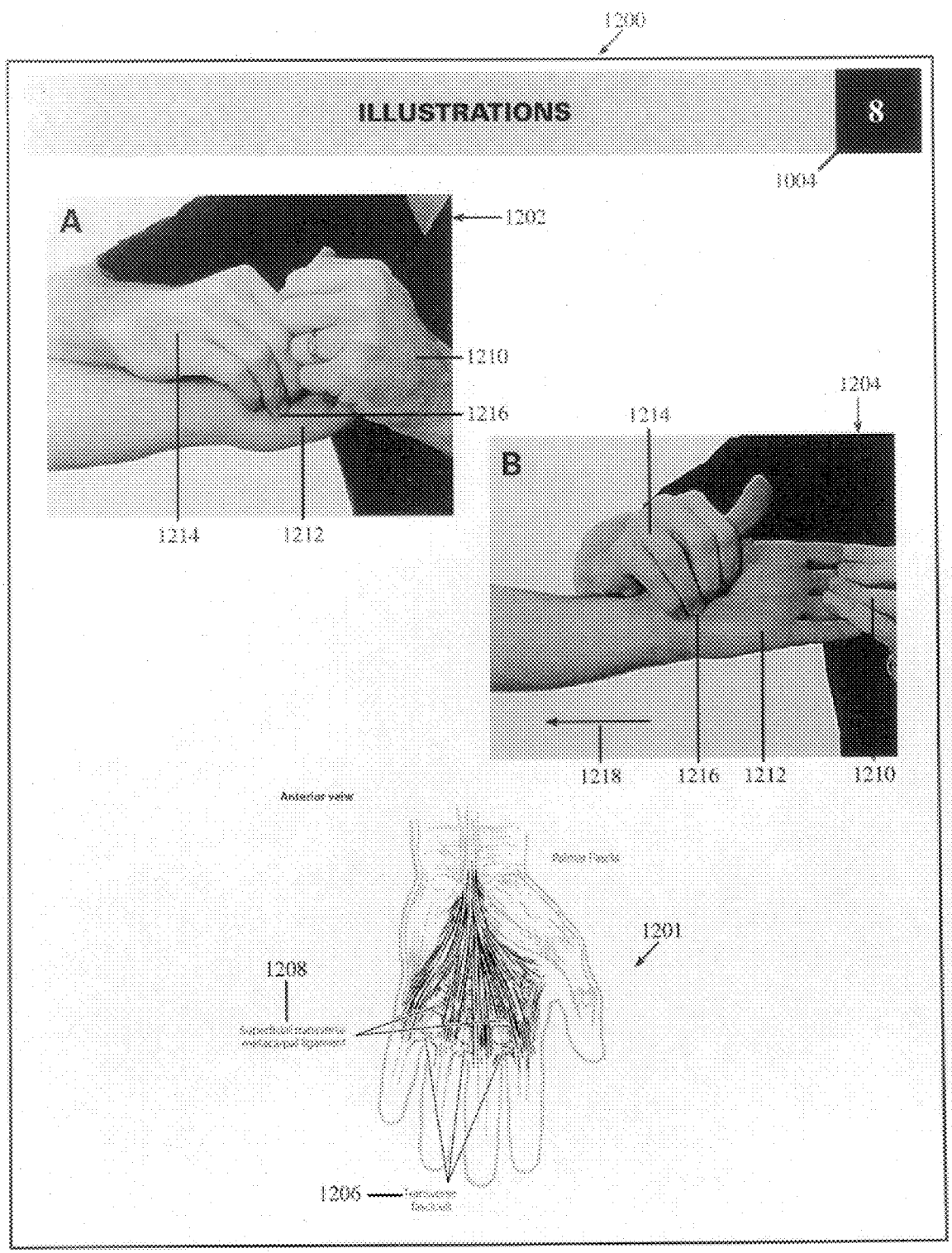
FIG. 12 depicts a second half of the expert treatment protocol used in combination with the first half shown in FIG. 11.

The medical practitioner who administers treatment optionally selects treatment protocol 8 as the first treatment protocol to be administered. FIGS. 11 and 12 depict treatment protocol 8. The features of FIG. 11 are numbered in like manner with respect to features that are described above with respect to FIG. 8, except the features of FIG. 11 are provided with an "a" postscript to show that the corresponding indicia to which the features of FIG. 11 apply have been adapted to provide a treatment protocol for adhesions of the palmar fascia.

FIG. 12 depicts indicia 1200 including an anatomical image 1201, as well as two photographs 1202 and 1204 showing soft tissue manipulation techniques for the features of anatomical image 1201. Anatomical image 1201 shows an anterior view of the palmar fascia with annotations 1206 and 1208 indicating the locations and longitudinal orientation of the superficial transverse metacarpal ligament and the transverse fasciculi.

Photographs 1202 and 1204 show the implementation of treatment protocol 812a (see FIG. 11). In photograph 1202, a medical practitioner's left hand 1210 is grasping the flexed fingers of a patient's hand 1212. Fingers of the medical practitioner's right hand 1214 are contacting the patient's palm to provide contact point 1216 at the back of the wrist above the palmar fascia shown in anatomical diagram 1201. The medical practitioner exerts passive motion on the patient's hand to extend the patient's fingers to the position shown in photograph 1204. The extension is done slowly over about five or more seconds. Tension on the palmar fascia is forced by the medical practitioner placing his or her thenar pads on the back of the wrist below the thumb.

The contact point 1216 described herein is preferably stationary, but if the practitioner feels extensive adhesions running the length of the superficial transverse metacarpal ligament, it is recommended to use a sliding contact during extension. This sliding contact runs in the direction of arrow 1218 from the knuckles towards the position of hand 1214 shown in photograph 1204. If median-nerve compression symptoms of numbness and tingling are duplicated, the medical practitioner stops treatment and begins again with a new grip att the back of the wrist with slightly less tension.

Patients usually experience significant improvements in just three or four visits spaced two days apart.

EXAMPLE 2

TREATMENT OF THE WRIST

ADHESIONS OF THE TRANSVERSE CARPAL LIGAMENT

Figure 13:
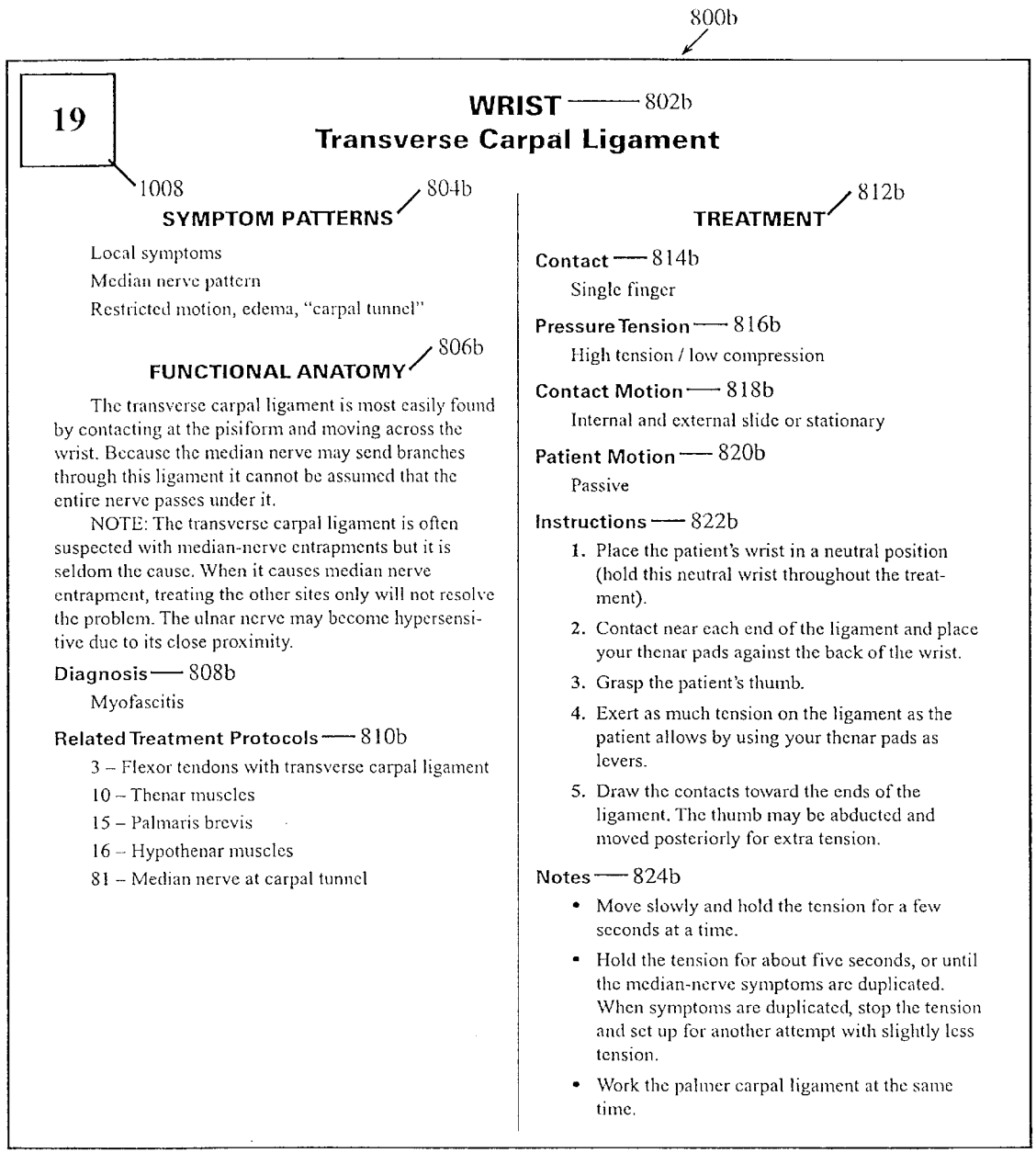
FIG. 13 depicts a treatment protocol for use in treating adhesions of the palmar fascia with symptoms corresponding to a another selected one of the FIG. 10 symptom pattern images.
Figure 14:
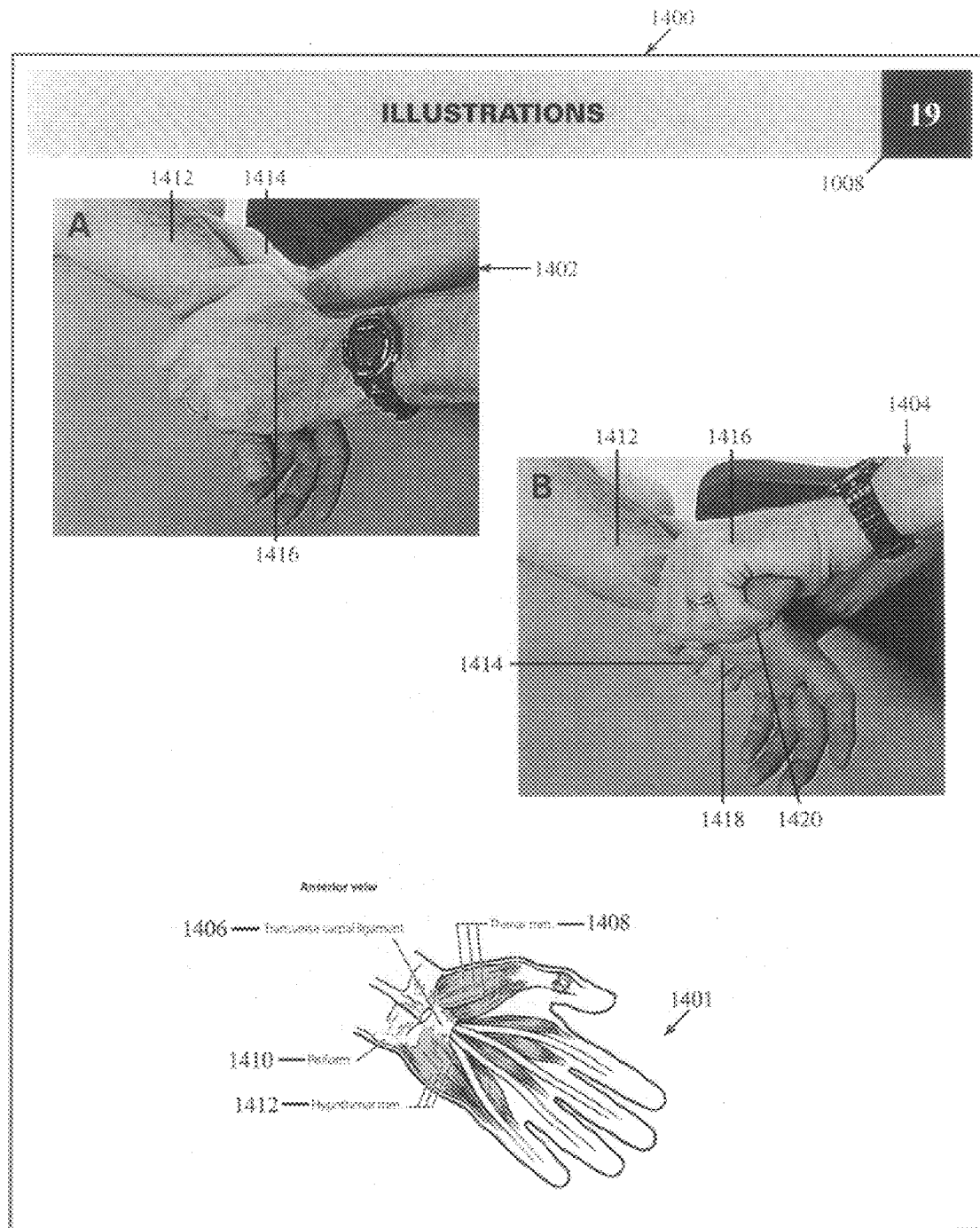
FIG. 14 depicts a second half of the expert treatment protocol of FIG. 14.

FIG. 10 shows symptom pattern image 1006 associated with indicator indicia 1008 referencing treatment protocols '3 and 19.' These treatment protocols are most likely to be selected by a patient having carpal tunnel symptoms brought on by carpal ligament entrapment of the median nerve. FIGS. 13 and 14 depict a treatment protocol '19' corresponding to indicator indicia 1008. The features of FIG. 13 are numbered in like manner with respect to features that are described above with respect to FIG. 8, except the features of FIG. 13 are provided with a "b" postscript to show that the corresponding indicia to which the features of FIG. 13 apply have been adapted to provide a treatment protocol for adhesions involving the carpal ligament.

FIG. 14 depicts indicia 1400 including an anatomical image 1401, as well as two photographs 1402 and 1404 showing soft tissue manipulation techniques for the features of anatomical image 1401. Anatomical image 1401 shows an anterior view of the transverse carpal ligament with annotations 1406, 1408, 1410, and 1412 indicating the respective locations and longitudinal orientations of the transverse carpal ligament, thenar muscles, pisiform, and hypothenar muscles.

Photograph 1402 shows a patient's wrist 1412 in a neutral position. This neutral wrist position is maintained throughout treatment. The medical practitioner's hands 1414 and 1416 are placed with their respective thenar pads at the back of the patients wrist 1412 to exert contact at each end of the transverse carpal ligament. Hand 1416 grasps the patients thumb. The medical practitioner's thenar pads are used as levers to exert as much tension as the patient permits at contact points 1418 and 1420. Photograph 1404 shows the ensuing extension motion with the fingers of hand 1414 contacting the area above the transverse carpal ligament and holding the same in tension with the posterior motion of the patient's thumb in hand 1416. This motion produces an internal stretch/sliding motion of the transverse carpal ligament, which is tensioned beneath contact points 1418 and 1420.

EXAMPLE 3

TREATMENT OF THE SHOULDER

ADHESIONS OF THE SUBSCAPULARIS

Figure 16:
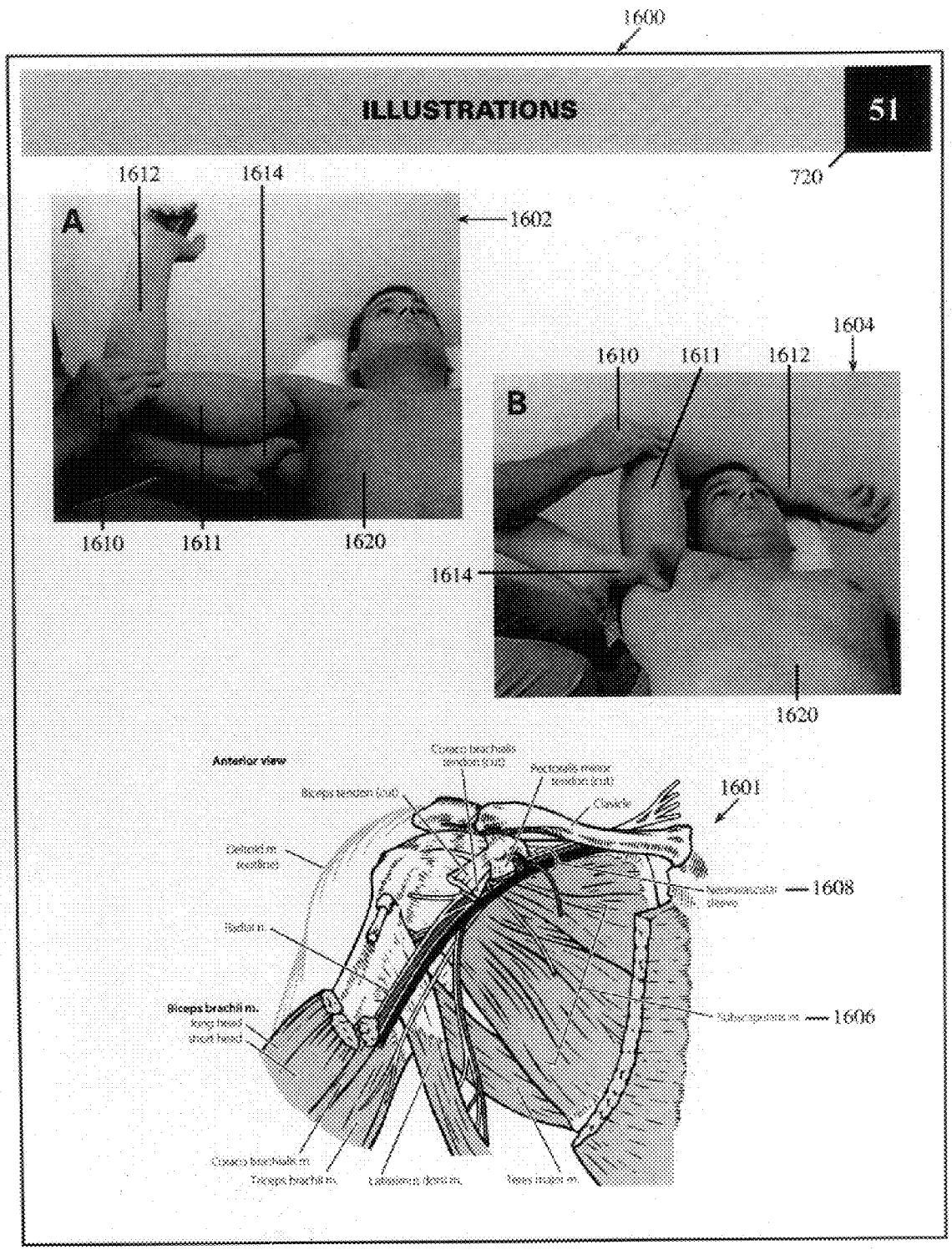
FIG. 16 depicts a preferred features of the FIG. 15 expert treatment protocol.

FIG. 7 shows symptom pattern image 718 and indicator indicia 720 referencing treatment protocols '48, 50, 51, 52, 54, 56, and 65.' Symptom pattern image 718 is most likely to be selected by people who routinely exert heavy pushing motions and competitive swimmers having instability of the rotator cuff and impingement syndrome. FIGS. 15 and 16 depict a treatment protocol '51' corresponding to a selected one of indicator indicia 720. The features of FIG. 15 are numbered in like manner with respect to features that are described above with respect to FIG. 8, except the features of FIG. 15 are provided with a "c" postscript to show that the corresponding indicia to which the features of FIG. 15 apply have been adapted to provide a treatment protocol for adhesions of the subscapularis.

FIG. 16 depicts indicia 1600 including an anatomical image 1601, as well as two photographs 1602 and 1604 showing soft tissue manipulation techniques for the features of anatomical image 1601. Anatomical image 1601 shows an anterior view of the subscapularis with a plurality of annotations, e.g. 1606 and 1608, indicating the respective locations and longitudinal orientations of anatomical features including the subscapularis and neurovascular sleeve.

Photograph 1602 shows a supine patient 1608. A medical practitioner's hand 1610 is grasping the patient's humerus 1611 to slightly abduct humerus 1611 to a comfortable position for the patient that relieves tension on the patient's subscapularis with the patient's elbow bent ninety degrees or more. The thumb of medical practitioner's hand 1614 has palpitated past the latissimus dorsi and teres major to the anterior surface of the scapula of patient 1608. The medical practitioners hand 1614 feels the entire surface of the patient 1608's scapula and moves superior to the brachial chords, then medial into the axilla. Hand 1614 provides a contact point inferior to the lesion by grasping as shown in photograph 1602. This grasping motion draws the skin and lose tissue of patient 1608 to a point just supro-lateral of the area to be manipulated. Hand 1610 subsequently abducts humerus 1611 over the patient's head to the position shown in photograph 1604 keeping the patient's elbow as far posterior as is possible. Patient 1608 is repeatedly returned to the position shown in photograph 1602, and is requested to make active motions to the position shown in photograph 1604.

EXAMPLE 4

TREATMENT OF THE SHOULDER

ADHESIONS OF THE INFRASPINATUS/TERES MINOR WITH DELTOID

Figure 17:
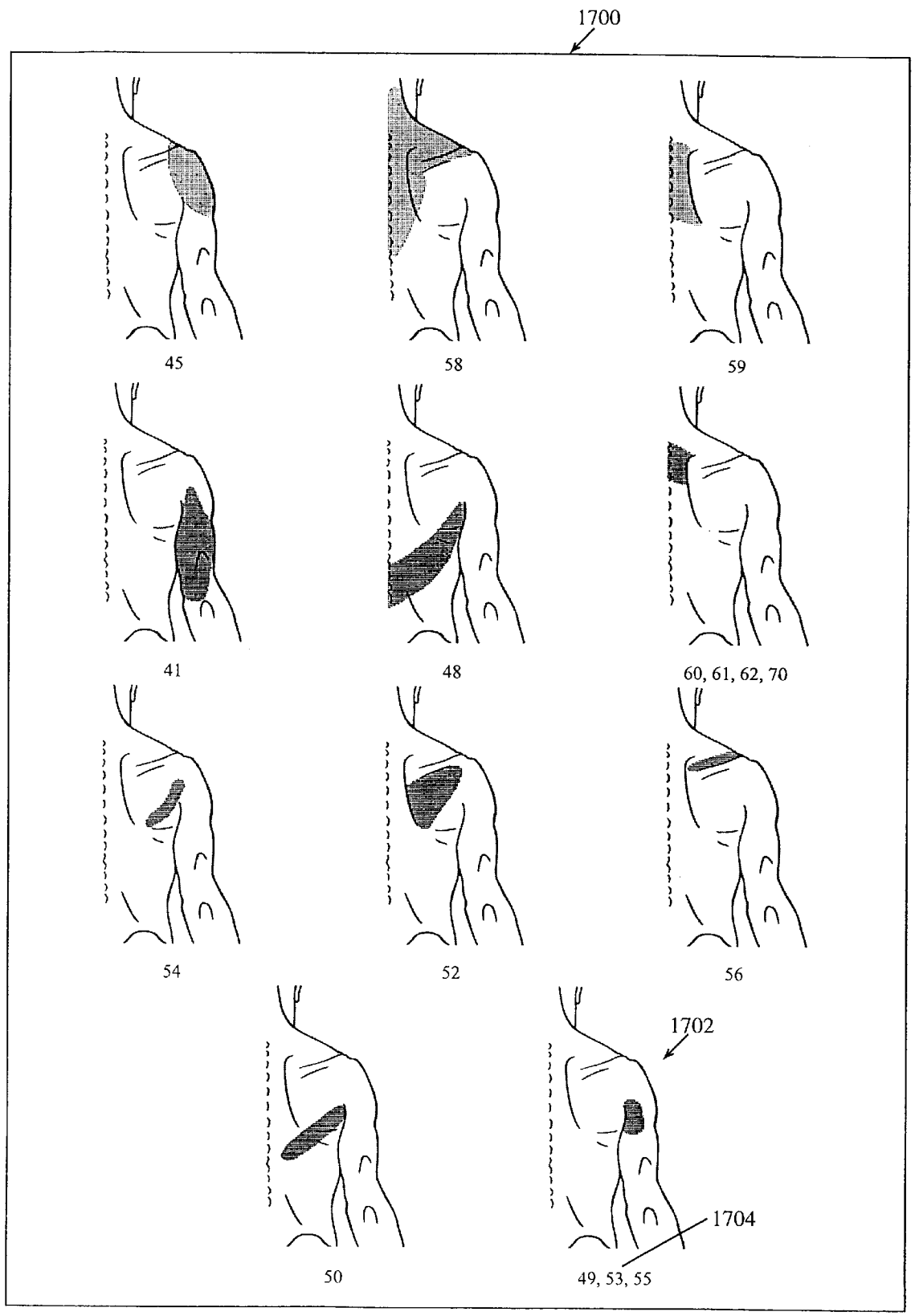
FIG. 17 depicts a plurality of anterior back and right arm symptom pattern images for use in the FIG. 6 process.

FIG. 17 depicts a plurality of symptom pattern images 1700 including symptom pattern image 1702, which is associated with indicator indicia 1704 including an identifier for treatment protocol '53.' Patients in need of this treatment protocol are those who have developed an adhesion at the lateral edge of the infraspinatus and teres minor, and the inferior edge of the posterior deltoid.

Figure 19:
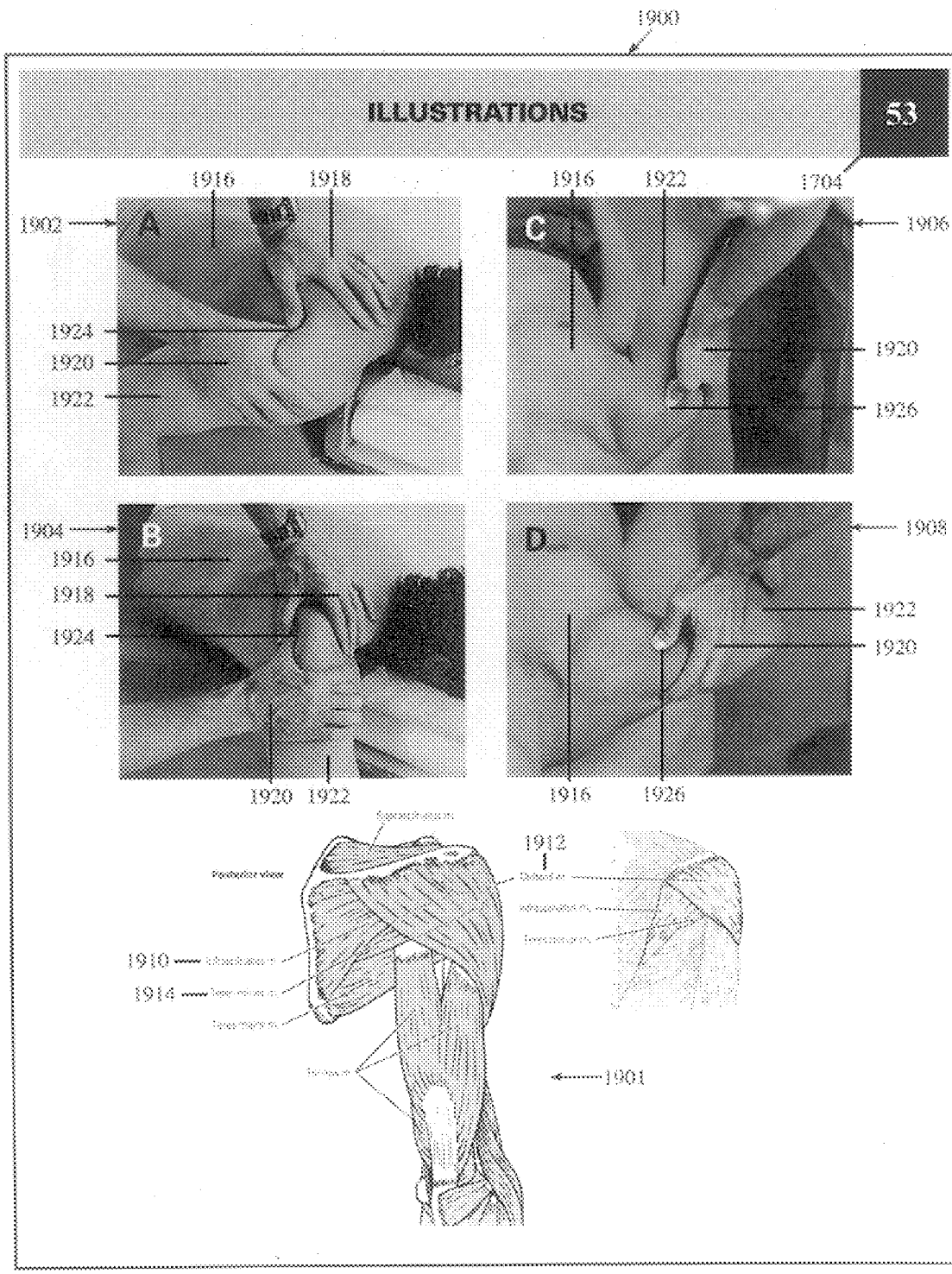
FIG. 19 depicts preferred features of the FIG. 18 treatment protocol.

FIGS. 18 and 19 depict a treatment protocol '53' corresponding to a selected one of indicator indicia 1704. The features of FIG. 18 are numbered in like manner with respect to features that are described above with respect to FIG. 8, except the features of FIG. 18 are provided with a "d" postscript to show that the corresponding indicia to which the features of FIG. 18 apply have been adapted to provide a treatment protocol for adhesions involving the infraspinatus/teres minor with deltoid.

FIG. 19 depicts indicia 1900 including an anatomical image 1901, as well as four photographs 1902,1904,1906, and 1908 showing soft tissue manipulation techniques for treating adhesions in the features of anatomical image 1901. Anatomical image 1901 shows a posterior view of the infraspinatus/teres minor with deltoid including a plurality of annotations, e.g. 1910, 1912, and 1914, indicating the respective locations and longitudinal orientations of anatomical features including the infraspinatus, teres minor, and deltoid.

Photograph 1902 shows a prone patient 1916. The patient's humerus 1922 is aducted. A medical practitioner's hands 1918 and 1920 are grasping the patient's shoulder to place the practitioner's thumbs in over contact point 1924, which lies just over the inferior edge of the patient's posterior deltoid. The contact point is moved as much as possible towards the teres minor, in order to draw tension medially. In photograph 1904, the patient has moved humerus 1922 to reach overhead, also in order to draw tension medially. This motion induces longitudinal sliding motion of the deltoid under tension beneath contact point 1924.

Photograph 1906 shows a supine patient 1916 who is about to undergo treatment of the infraspinatus under deltoid after the procedures of photographs 1902 and 1904 have been performed about three to five times. The patients humerus 1922 is flexed forward and externally rotated in an upwards direction. The medical practitioner's thumb is placed on contact point 1926 over the patient's deltoid at a location just anterior to the infraspinatus to traction the deltoid posterior along the fibers of the infraspinatus. The patient is requested to actively rotate the humerus between upward and downward positions. Photograph 1908 shows rotation to a downward position.

EXAMPLE 5

TREATMENT OF THE NERVES

ADHESIONS OF THE BRACHIAL CHORDS AT THE SUBSCAPULARIS

Figure 20:
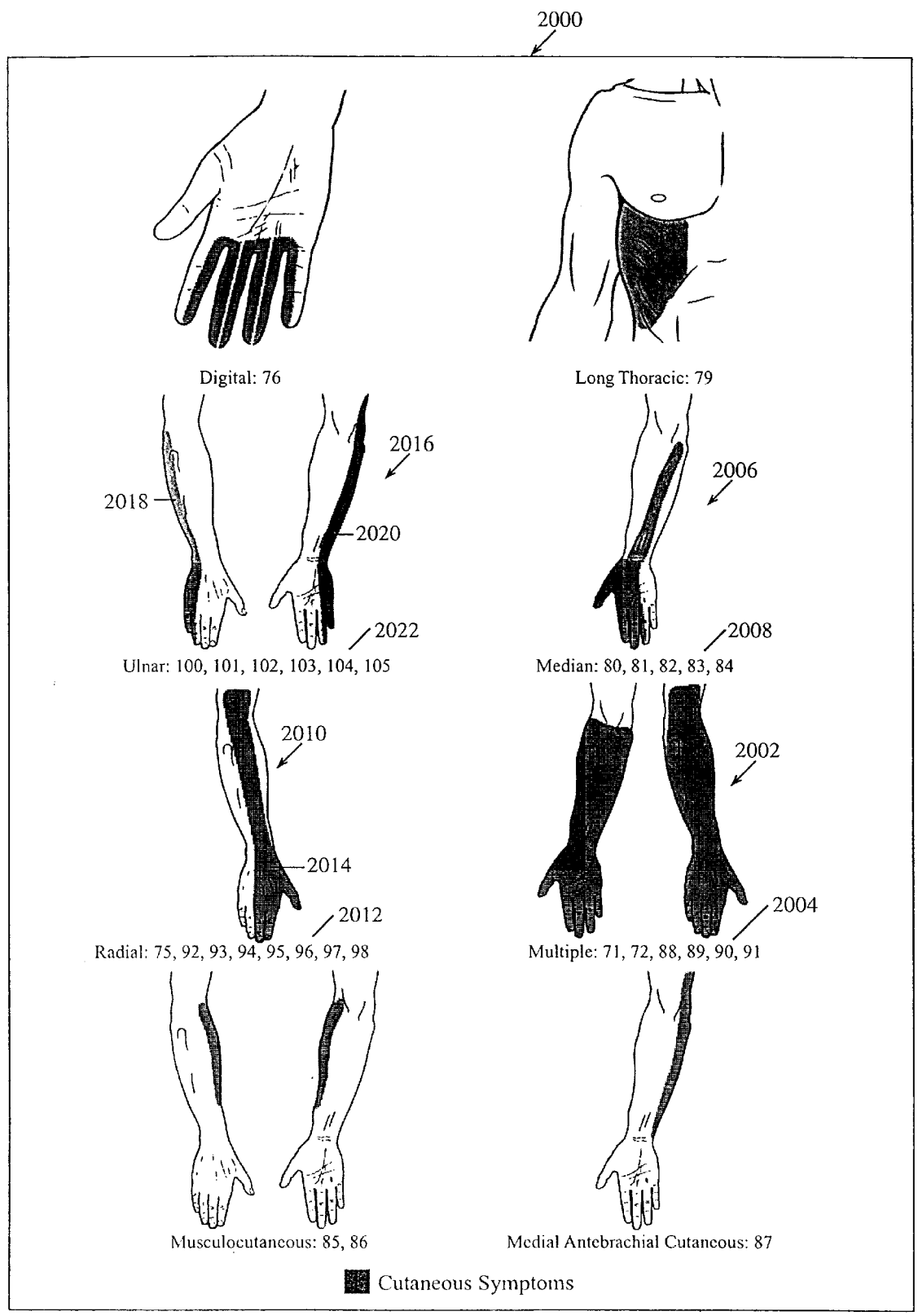
FIG. 20 depicts a plurality of symptom pattern images for use in the FIG. 6 process, wherein the symptom pattern images represent cutaneous symptoms indicative of nerve involvement.

FIG. 20 shows a plurality of nerve symptom pattern images 2000 including symptom pattern image 2002 showing that the patients whole hand is affected by pain, numbness or tingling sensations. Symptom pattern image 2002 is associated with indicator indicia 2004 identifying a plurality of treatment protocols including protocol '71.' This treatment protocol is most likely to be selected by people who have an entrapment of the brachial chords of the brachial plexus at the subscapularis.

Figure 22:
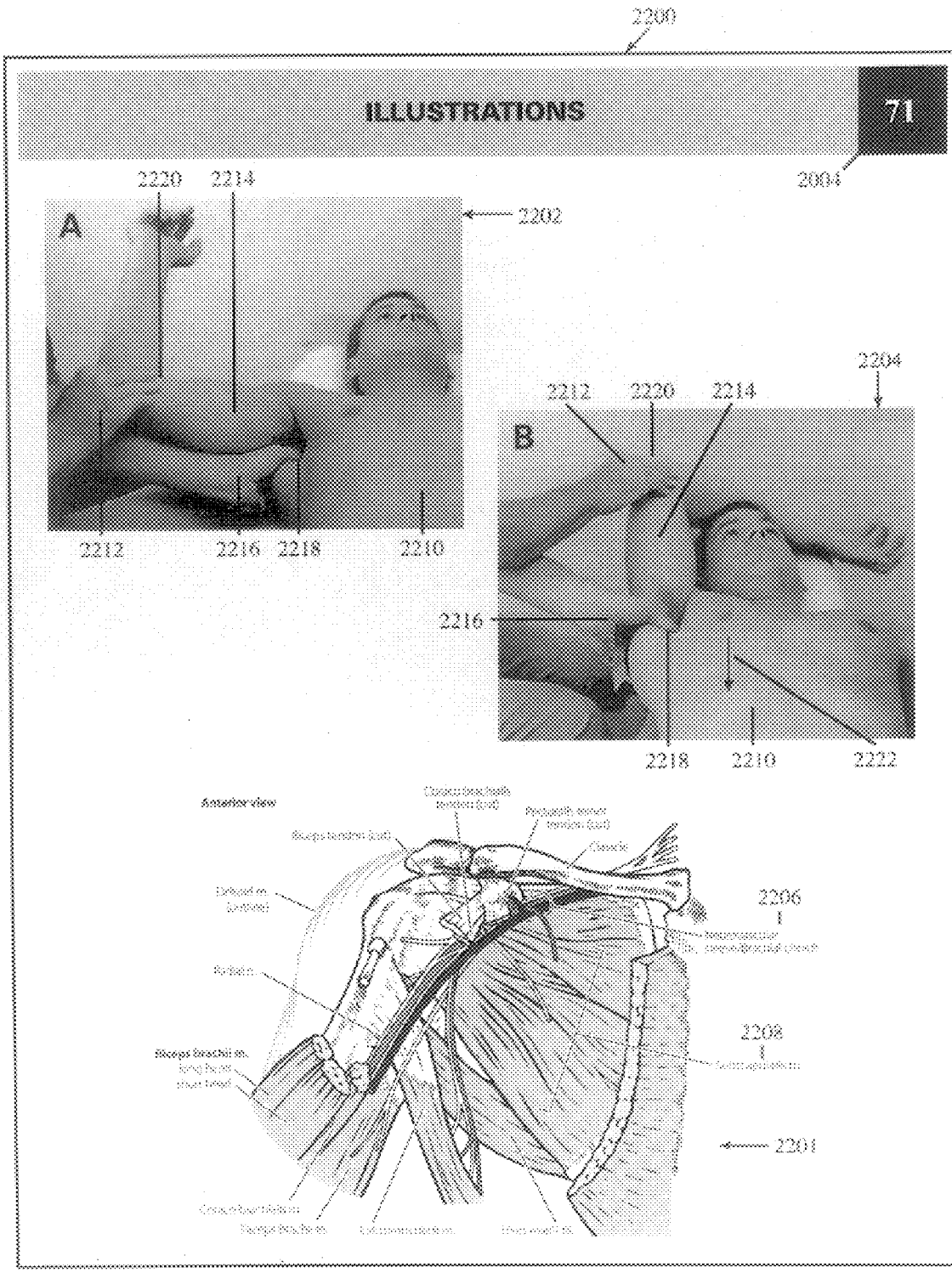
FIG. 22 depicts preferred features of the FIG. 21 treatment protocol.

FIGS. 21 and 22 depict a treatment protocol '71' corresponding to a selected one of indicator indicia 2004. The features of FIG. 21 are numbered in like manner with respect to features that are described above with respect to FIG. 8, except the features of FIG. 21 are provided with an "e" postscript to show that the corresponding indicia to which the features of FIG. 21 apply have been adapted to provide a treatment protocol for adhesions of the brachial chords at the subscapularis.

FIG. 22 depicts indicia 2200 including an anatomical image 2201, as well as two photographs 2202 and 2204 showing soft tissue manipulation techniques for the features of anatomical image 2201. Anatomical image 2201 shows an anterior view of the brachial chords proximate the subscapularis with annotations, e.g. 2206 and 2208, indicating the respective locations and longitudinal orientations of anatomical features including the subscapularis and neurovascular sleeve/brachial chords.

Photograph 2202 shows a supine patient 2210. A medical practitioner's hand 2212 is grasping the patient's humerus 2214 to slightly abduct humerus 2214 to an extended side position that relieves tension on the patient's subscapularis with the patient's elbow bent ninety degrees or more. The thumb of medical practitioner's hand 2216 has palpitated past the latissimus dorsi and teres major to the anterior surface of the scapula of patient 2210, then moved superior to the brachial chords. Hand 2216 provides a contact point 2218 inferior to the lesion by grasping as shown in photograph 2202. This grasping motion draws the skin and lose tissue of patient 2210 to a point between the muscle and nerve tissue and exerts tension along the nerve/muscle junction. Photograph 2204 shows the position of patient 2210 after abduction of the humerus 2214 to an overhead position with the elbow 2220 of patient 2210 placed in as far a posterior position as the patient will allow. During abduction of the humerus 2214, it is preferred to maintain contact point 2218 in a stationary position until the medical practitioner feels tension developing beneath contact point 2218. After this tension develops, it is preferred that the medical practitioner slide hand 2216 and contact point 2218 in the downward direction of arrow 2222 to optimize tension. This motion produces longitudinal sliding motion of the neurovascular sleeve and brachial chords beneath contact point 2218.

EXAMPLE 6

TREATMENT OF THE SHOULDER

ADHESIONS OF THE DORSAL SCAPULAR NERVE AT THE SERRATUS POSTERIOR SUPERIOR

Figure 23:
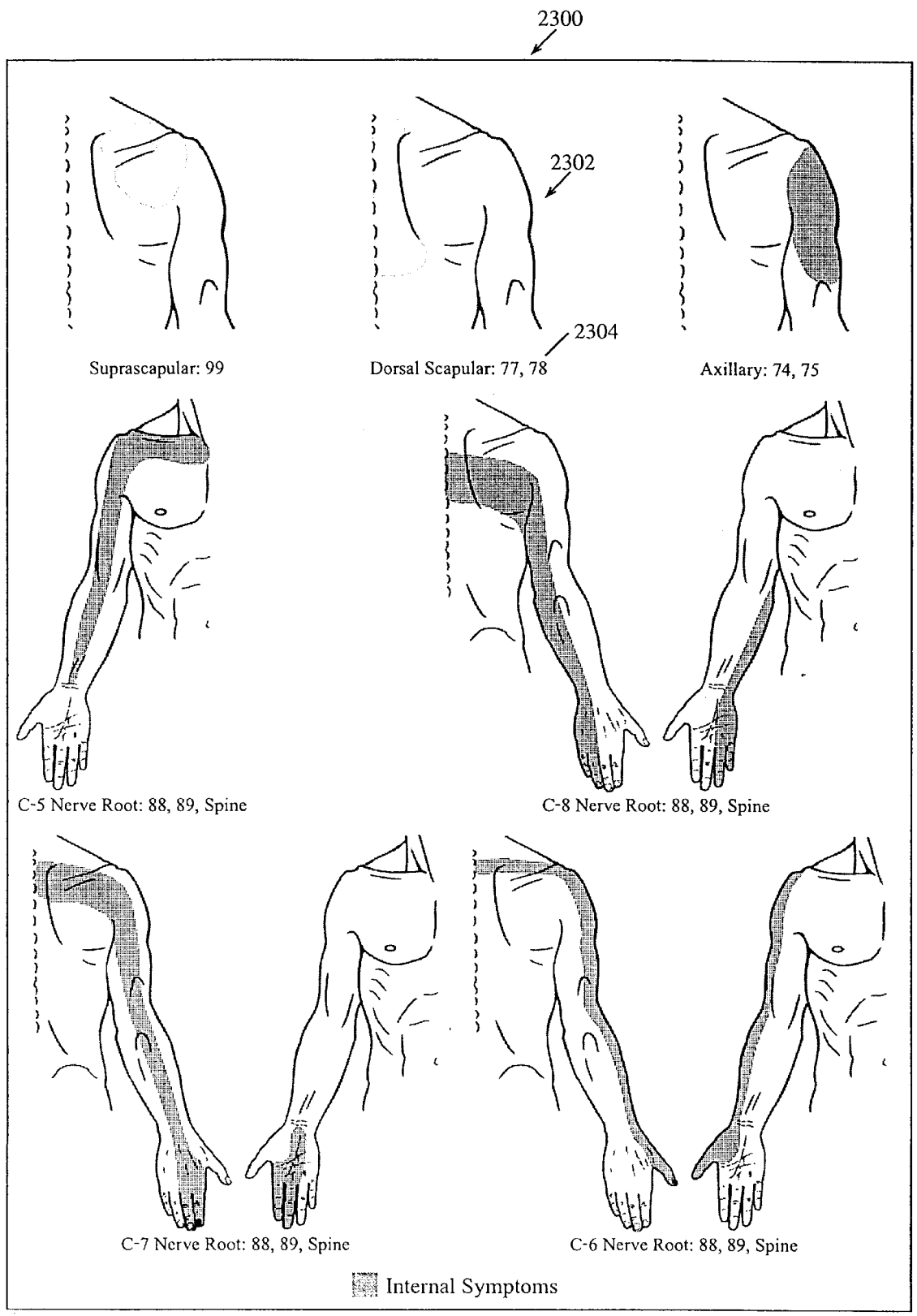
FIG. 23 depicts a plurality of symptom pattern images for use in the FIG. 6 process, wherein the symptom pattern images represent internal symptoms indicative of nerve involvement.

FIG. 23 shows a plurality of nerve symptom pattern images 2300 including symptom pattern image 2302 showing that the patient's central back is affected by pain, numbness or tingling sensations. Symptom pattern image 2302 is associated with indicator indicia 2304 identifying a plurality of treatment protocols including protocol '77' and protocol '78.' In this case one or both treatment protocols can be performed.

Figure 24:
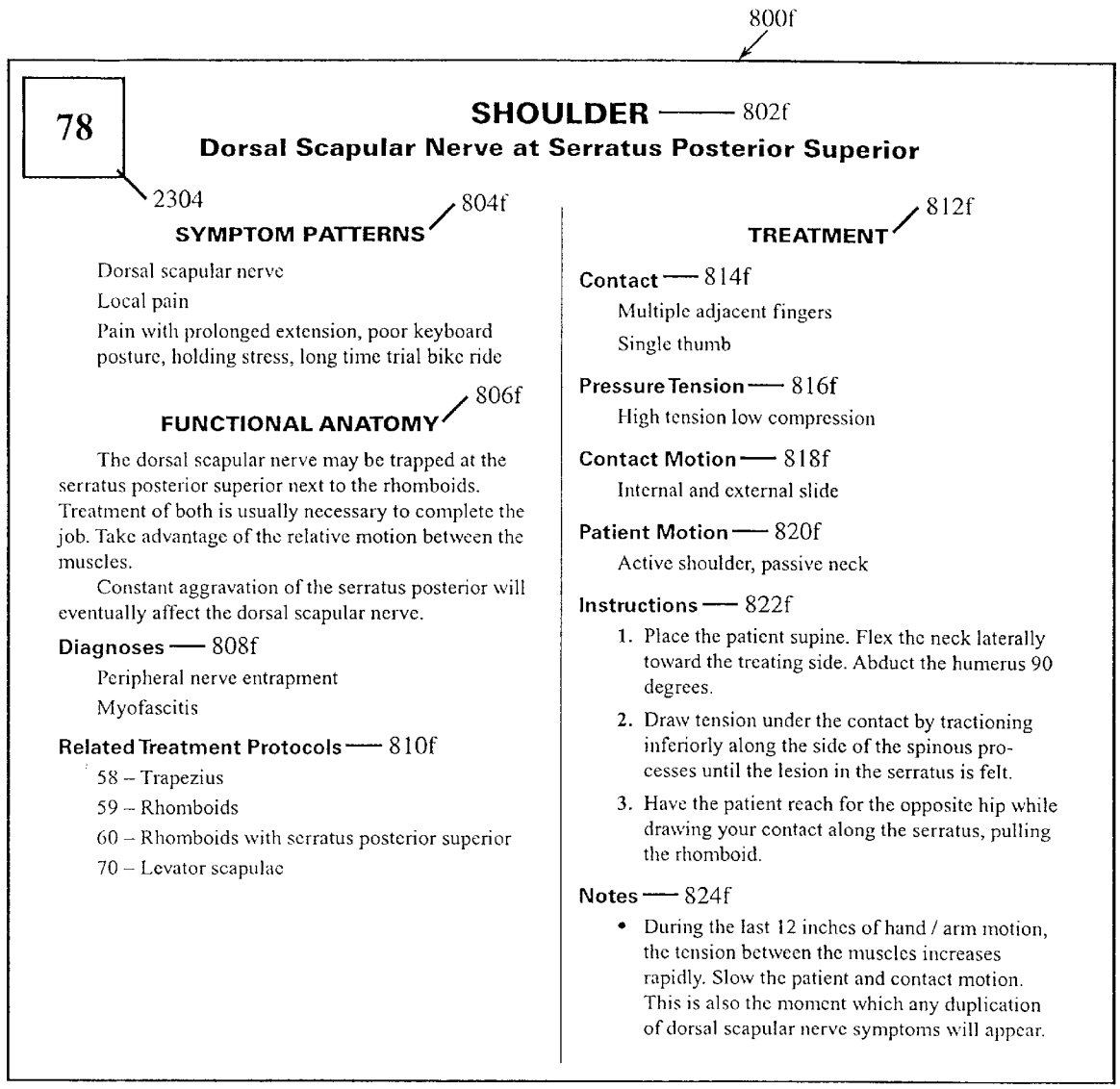
FIG. 24 depicts a treatment protocol for use in the FIG. 6 process corresponding to the FIG. 23 symptom pattern images.

FIG. 24 depicts treatment protocol '78,' which is used to treat adhesions of the dorsal scapular nerve at the serratus posterior superior. This treatment protocol is most likely to be selected by people who have an entrapment of the dorsal scapular nerve at the serratus posterior superior. The features of FIG. 24 are numbered in like manner with respect to features that are described above with respect to FIG. 8, except the features of FIG. 24 are provided with a "f" postscript to show that the corresponding indicia to which the features of FIG. 24 apply have been adapted to provide a treatment protocol for adhesions of the dorsal scapular nerve at the serratus posterior superior.

Figure 25:
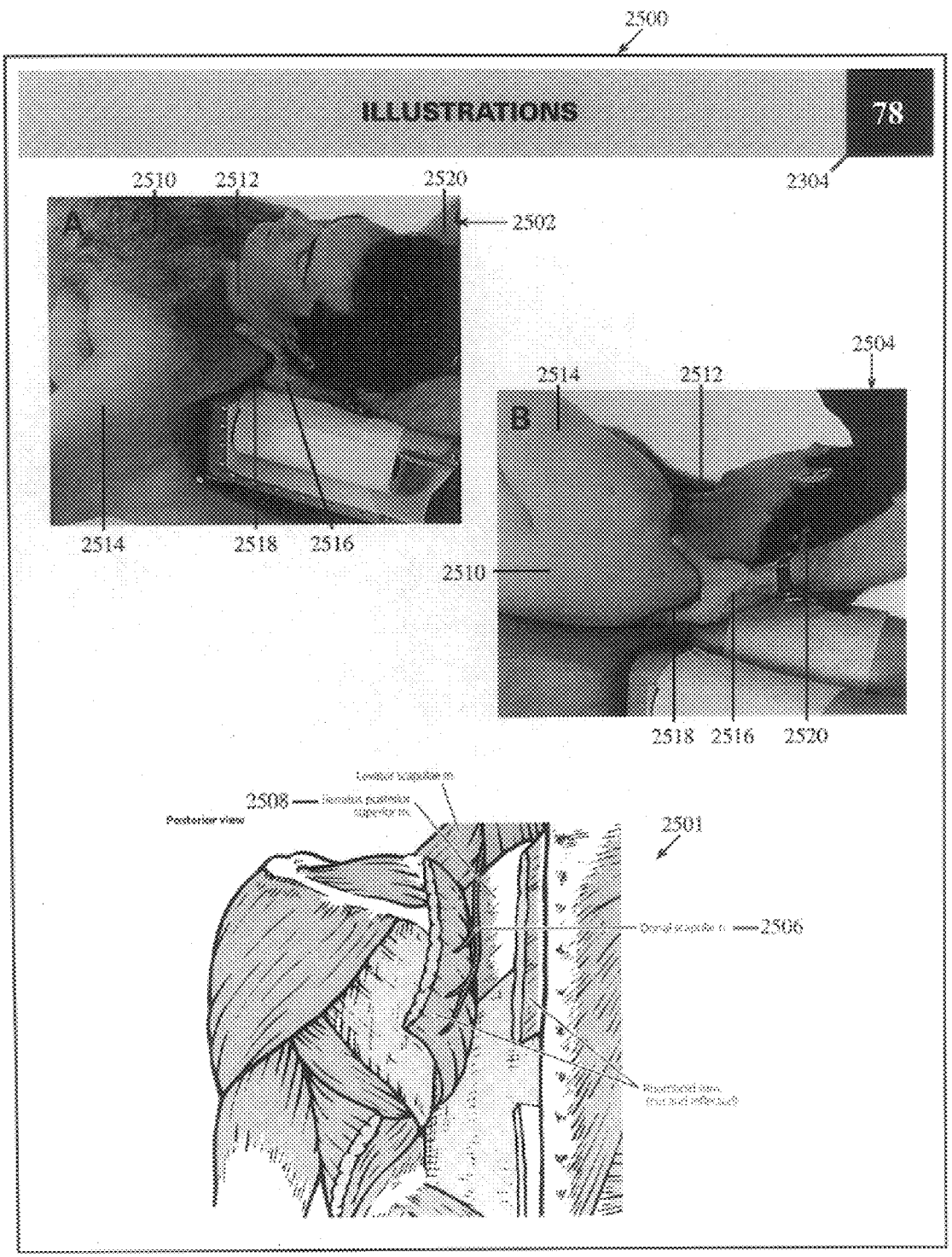
FIG. 25 depicts preferred features of the FIG. 24 treatment protocol.

FIG. 25 depicts indicia 2500 including an anatomical image 2501, as well as two photographs 2502 and 2504 showing soft tissue manipulation techniques for the features of anatomical image 2501. Anatomical image 2501 shows a posterior view of the dorsal scapular nerve proximate the serratus posterior superior muscle with annotations, e.g. 2506 and 2208, indicating the respective locations and longitudinal orientations of anatomical features including the dorsal scapular nerve and the serratus posterior superior muscle.

Photograph 2502 shows a supine patient 2510 with neck 2512 inclined laterally toward the left, i.e., toward the side where symptoms are felt. The patient's humerus 2514 is abducted 90°. A medical practitioner's hand 2516 is grasping patient 2512 at a contact point 2518 over the patient's levator scapulae muscles. Tension is drawn at the contact point by tractioning hand 2512 and contact point 2516 inferiorly along the side of the patient's spinous processes until the medical practitioner feels an adhesion in the serratus posterior superior muscle. As shown in photograph 2504, patient 2510 is then requested to move humerus in a motion as though the patent is reaching for the opposite (right) hip. At the same time, the medical practitioner draws contact point 2518 and hand 2512 laterally along the serratus posterior superior muscle. Hand 2520 passively moves the patient's head to the right as shown in photograph 2504. These movements pull on the patient's rhomboid muscle. The patient is requested to slow down the last twelve inches of arm motion towards the opposite hip because the serratus muscle tension increases rapidly in this range of motion. This last twelve inches of motion is also the range in which the treatment is most likely to duplicate the patient's symptoms. The motion is made with high tension and low compression provided beneath contact point 2518 by the fingers and thumb of hand 2512. The motion causes simultaneous longitudinal sliding motion under tension of the dorsal scapular nerve and the serratus posterior superior muscle with respect to contact point 2518.

EXAMPLE 7

TREATMENT OF THE FOREARM

ADHESIONS OF THE MEDIAN NERVE AT THE PRONATOR TERES

FIG. 20 shows a plurality of nerve symptom pattern images 2000 including symptom pattern image 2002 corresponding to a plurality of treatment protocol indicia 2008 including an indicia for protocol '83.' Persons in need of protcol '83' are those having pain, numbness or tingling sensations of the lower anterior arm and the first three digits.

Figure 26:
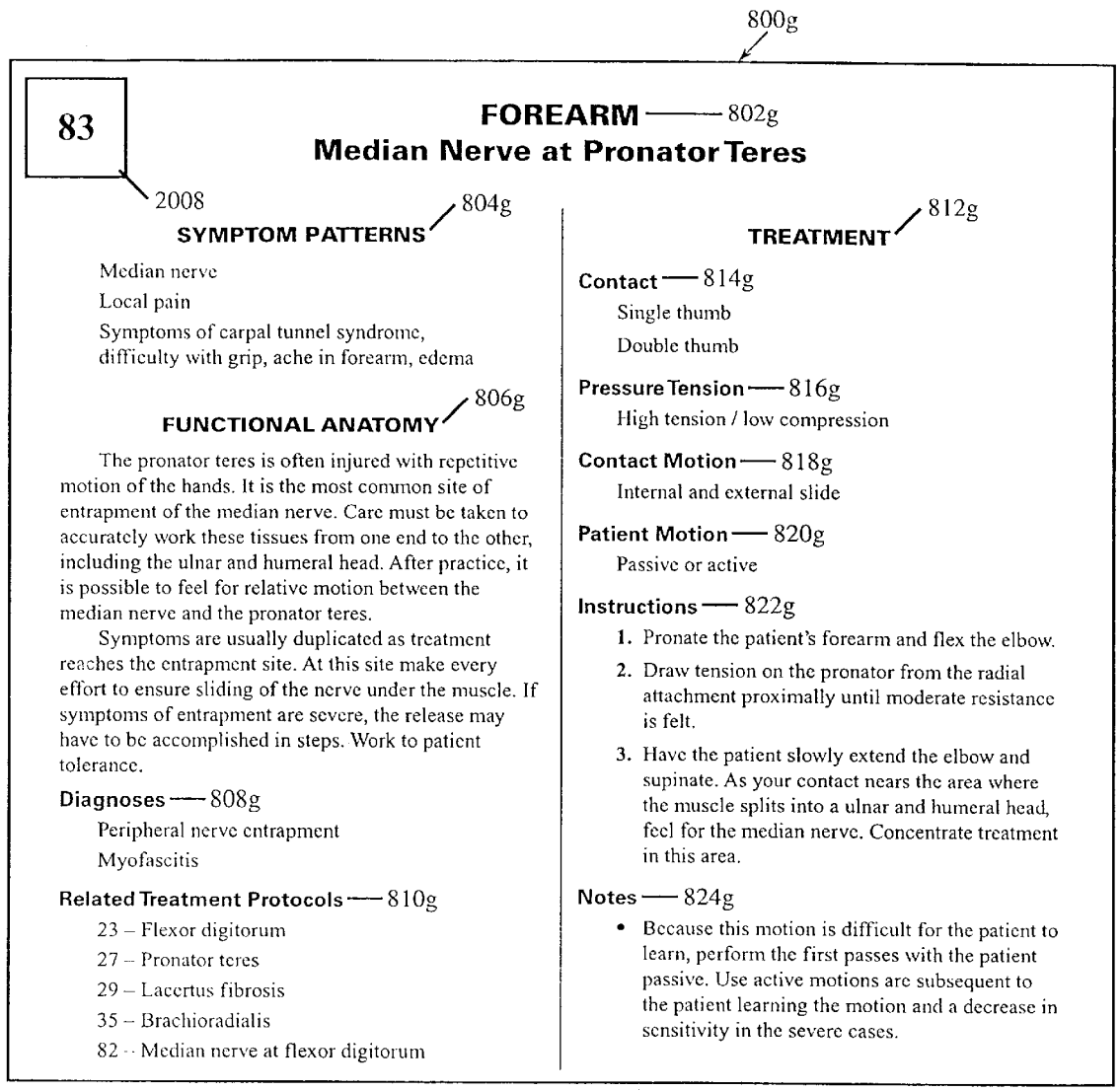
FIG. 26 depicts another treatment protocol for use in the FIG. 6 process corresponding to the FIG. 20 symptom pattern images.

FIG. 26 depicts treatment protocol '83,' which is designed to treat adhesions of the median nerve at the pronator teres. The features of FIG. 26 are numbered in like manner with respect to features that are described above in FIG. 8, except the features of FIG. 28 are provided with a "g" postscript to show that the corresponding indicia to which the features of FIG. 28 apply have been adapted to provide a treatment protocol for adhesions of the median nerve at the pronator teres.

Figure 27:
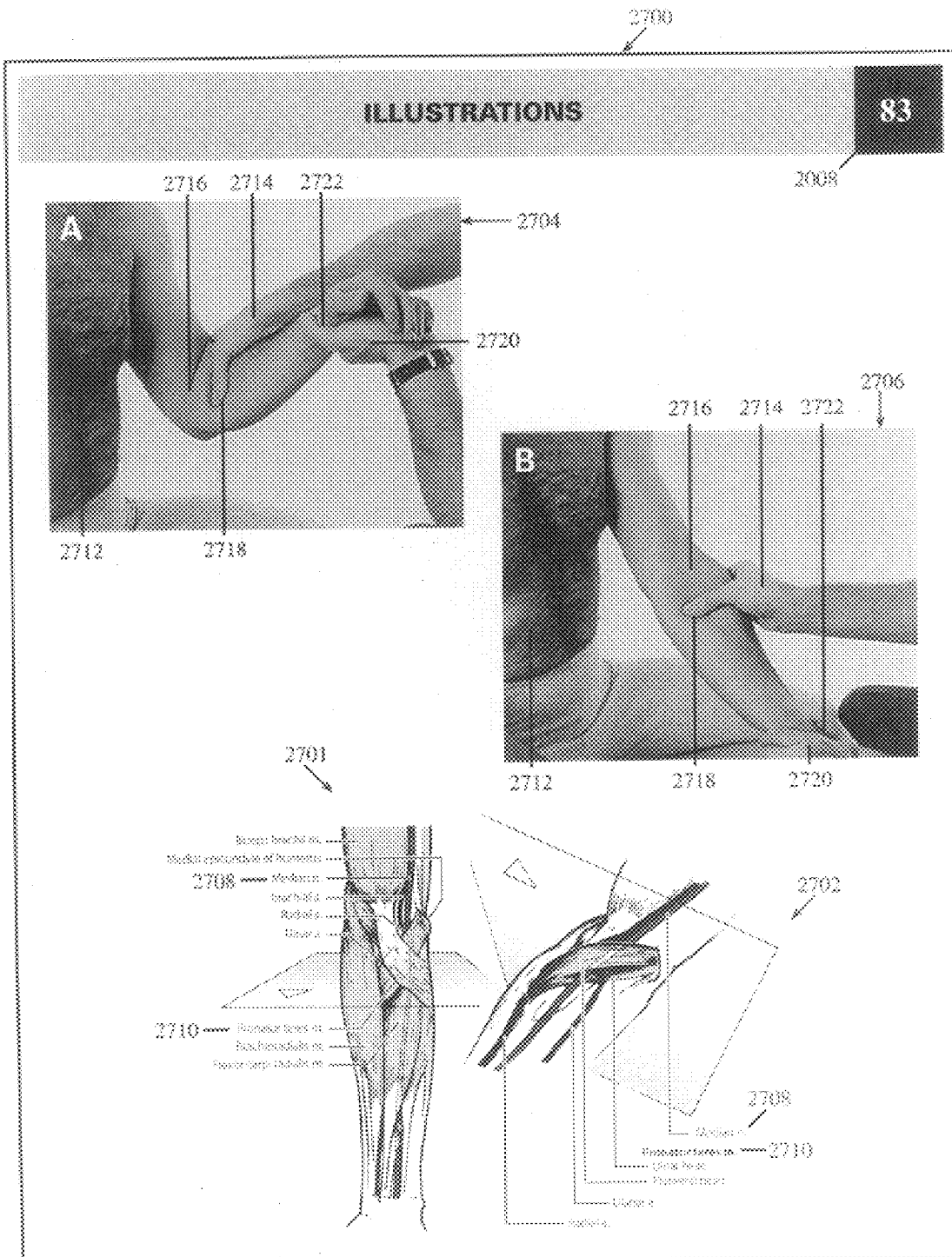
FIG. 27 depicts preferred features of the FIG. 26 treatment protocol.

FIG. 27 depicts indicia 2700 including anatomical images 2701 and 2702, as well as two photographs 2704 and 2706 showing soft tissue manipulation techniques for the features of anatomical images 2701 and 2702. Anatomical images 2701 and 2702 show a plurality of annotations, e.g., 2708 indicating the median nerve and annotation 2710 indicating the pronator teres muscle.

Photograph 2704 shows a patient 2712 seated in an upright position. Medical practitioner's hand 2714 is grasping the patient's elbow 2716 to provide contact point 2718. Hand 2720 grasps the patient's wrist at contact point 2722. Hands 2714 and 2720 pronate the patient's forearm and flex the elbow as shown in photograph 2704. Hand 2714 moves contact point 2718 proximally in a medial motion along the pronator teres until moderate resistance is felt. The patient is requested to slowly extend the elbow and supinate to the position shown in photograph 2706. The medical practitioner feels for the median nerve in the area shown as contact point 2728 in photograph 2706 where the pronator teres separates into an ulnar head and a humeral head. The patients bending motion produces high tension and low compression beneath contact points 2718. The elbow is then pronated and bent to the position of photograph 2704, and the motion to the position of photograph 2706 is repeated. it is recommended that the first few passes be made with passive motion on the patient;'s part because it is difficult for the patient to learn the correct motion between photographs 2704 and 2706. The motion causes tensile longitudinal sliding motion of the median nerve and pronator teres with respect to contact point 2718.

EXAMPLE 8

TREATMENT OF THE SHOULDER, ARM AND HAND

ADHESIONS OF THE NEUROVASCULAR SLEEVE AT THE CORACO-PECTORAL TUNNEL

FIG. 20 shows a plurality of nerve symptom pattern images 2000 including symptom pattern image 2002 showing that the patient's skin of the lower arm and hand is affected by pain, numbness or tingling sensations. Indicia 2004 includes reference to treatment protocol '90.' Protocol '90' may be implemented either before or after the treatment protocol '71' described in Example 5 for the same cutaneous symptoms shown in symptom pattern image 2002. Persons in need of protocol '90' are those having the skin of the entire lower arm afflicted by pain, numbness or tingling sensations.

FIG. 28 depicts treatment protocol '90,' which is designed to treat adhesions of the neurovascular sleeve at the coraco-pectoral tunnel. This treatment protocol is most likely to be selected for people who have adhesions with multiple nerve involvement affecting the entire lower arm and an entrapment of the neurovascular sleeve at the coraco-pectoral tunnel. The features of FIG. 28 are numbered in like manner with respect to features that are described above with respect to FIG. 8, except the features of FIG. 28 are provided with a "h" postscript to show that the corresponding indicia to which the features of FIG. 28 apply have been adapted to provide a treatment protocol for adhesions of the neurovascular sleeve at the coraco-pectoral tunnel.

Figure 29:
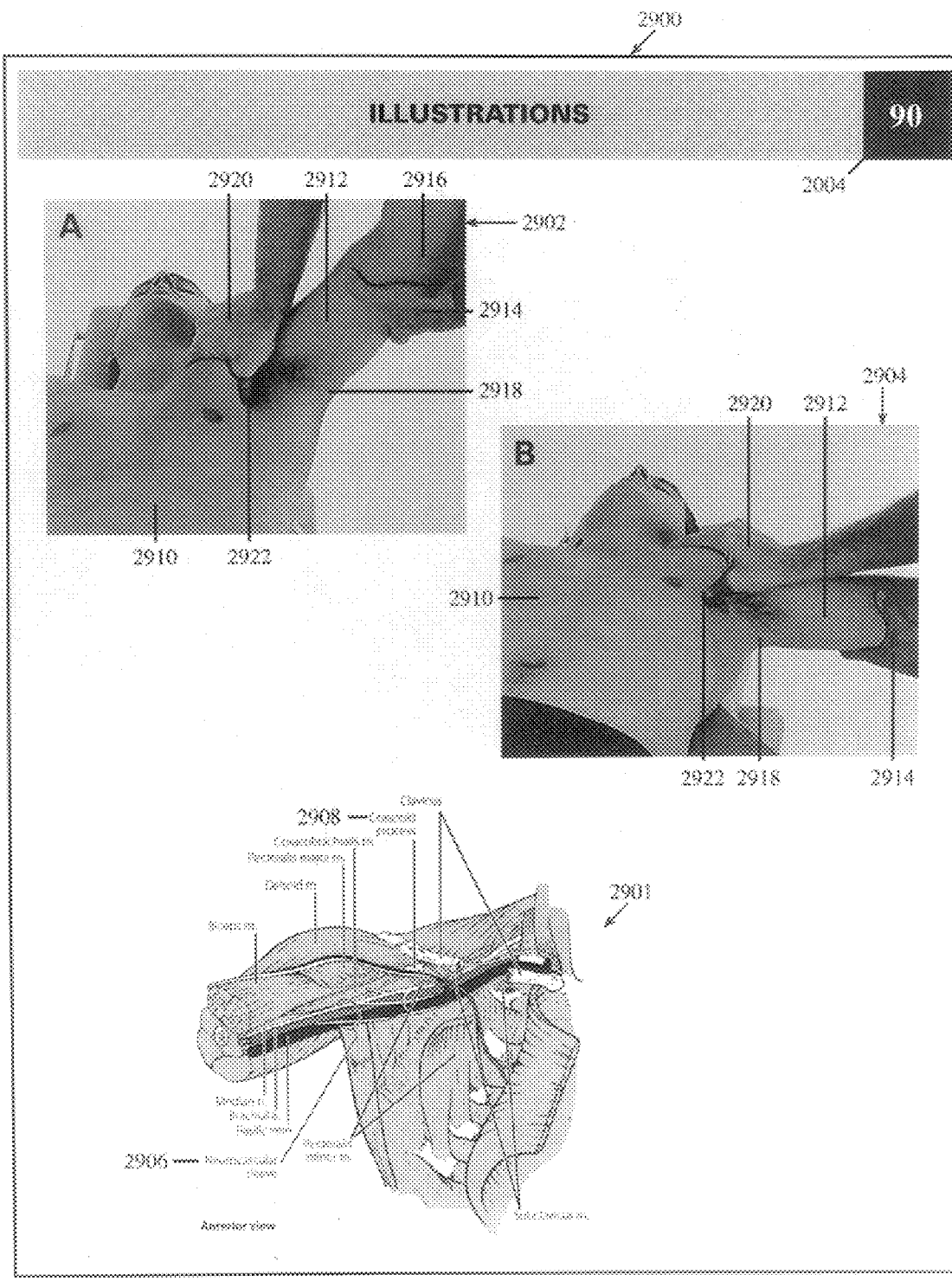
FIG. 29 depicts preferred features of the FIG. 28 treatment protocol.

FIG. 29 depicts indicia 2900 including an anatomical image 2901, as well as two photographs 2902 and 2904 showing soft tissue manipulation techniques for the features of anatomical image 2901. Anatomical image 2901 shows an anterior view of the neurovascular sleeve at the coraco-pectoral tunnel with annotations, e.g. 2906 and 2908, indicating the respective locations and longitudinal orientations of anatomical features including the neurovascular sleeve and the coracobrachialis muscle.

Photograph 2902 shows a supine patient 2910 with a forward flexed and slightly abducted humerus 2912. Medical practitioner's hand 2914 is supporting the patients arm with a firm grasp. Elbow 2916 is flexed 90° or more, and humerus 2912 is not externally rotated. Shoulder 2918 is protracted. The thumb of medical practitioner's hand 2920 palpitates along the posterior side of the patient's pectoralis minor to the neurovascular sleeve 2906 and the coracoid process where the thumb provides contact point 2922. Contact point 2922 is preferably located between the coracoid process and neurovascular sleeve at a position as far as possible towards the first rib and scalenes of patient 2910. The patient is requested to abduct humerus 2912 towards a position having more than 90° abduction, full retraction, and maximum posterior extension, as shown in photograph 2904. Contact point 2922 and the thumb of hand 2920 are moved in a supro-medial direction concomitantly with the abduction of humerus 2912 to the position shown in photograph 2904. This abduction together with supro-lateral motion of contact point 2922 provide a medial sliding motion of contact point 2922 with respect to the neurovascular sleeve 2906 proximal to the coracoid process 2908.

EXAMPLE 9

TREATMENT OF THE WRIST AND FOREARM

ADHESIONS OF THE RADIAL NERVE AT THE DISTAL BRACHIORADIALIS

FIG. 20 includes a symptom pattern image 2010 showing that a portion 2014 of the patient's lower arm and hand is affected by pain, numbness or tingling sensations. Symptom pattern image 2010 is associated with indicator indicia 2012 identifying a plurality of treatment protocols including protocol '92.'

FIG. 30 depicts treatment protocol '92,' which is designed to treat adhesions of the radial nerve at the distal brachioradialis. This treatment protocol is most likely to be selected by people who have difficulty in grasp and lift motions caused by an entrapment of the radial nerve. The features of FIG. 30 are numbered in like manner with respect to features that are described above with respect to FIG. 8, except the features of FIG. 30 are provided with an "I" postscript to show that the corresponding indicia to which the features of FIG. 30 apply have been adapted to provide a treatment protocol for adhesions affecting the radial nerve at the distal brachioradialis.

Figure 31:
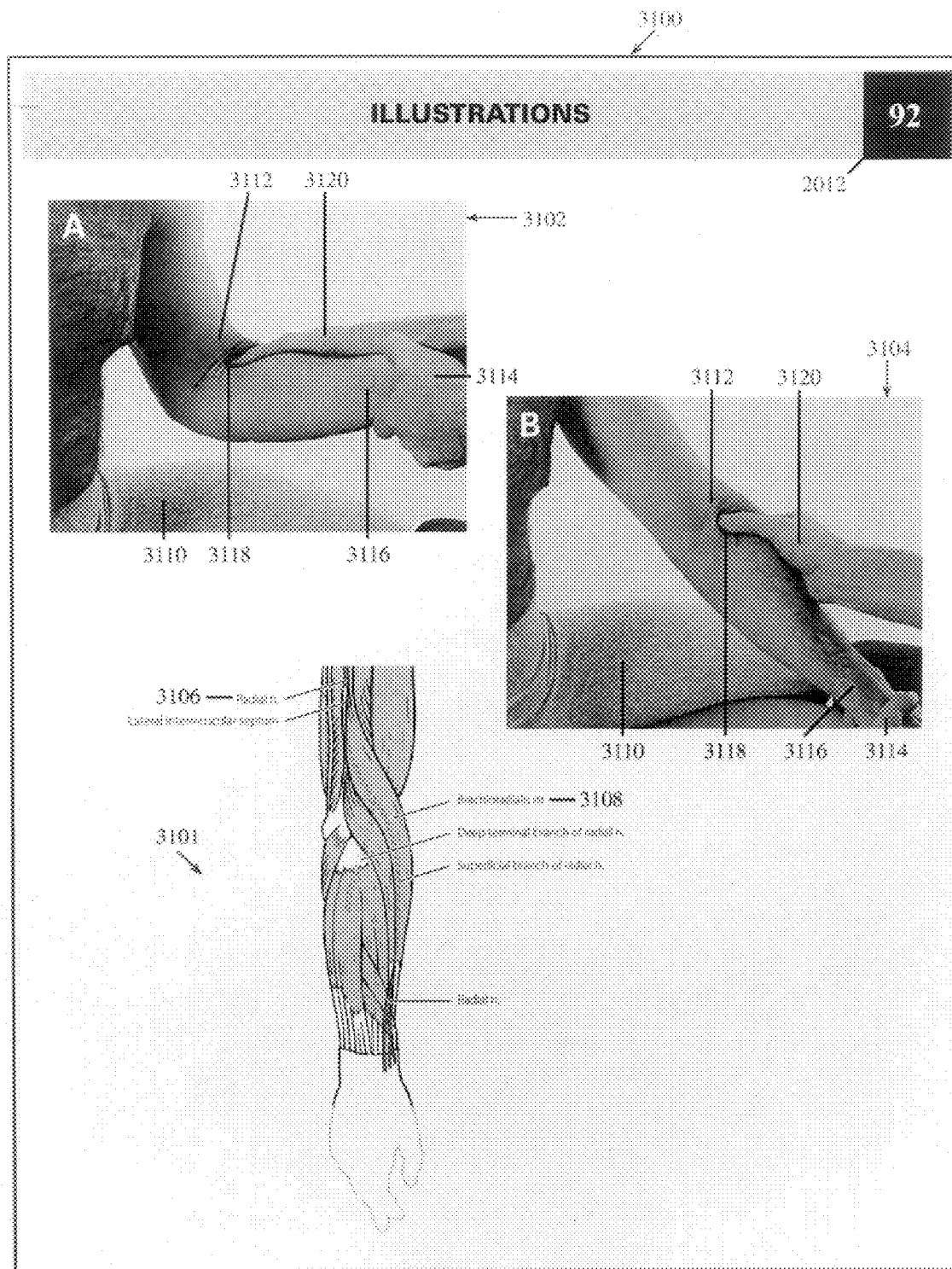
FIG. 31 depicts preferred features of the FIG. 30 treatment protocol.

FIG. 31 depicts indicia 3100 including an anatomical image 3101, as well as two photographs 3102 and 3104 showing soft tissue manipulation techniques for the features of anatomical image 3101. Anatomical image 3101 contains indicia annotating the features of anatomical image 3101, e.g., those for the radial nerve 3106 and the brachioradialis muscle 3108. These features also show the respective locations and longitudinal orientations of anatomical features on the lower arm.

Photograph 3102 shows a seated patient 3110 with elbow 3112 flexed about 90°. Medical practitioner's hand 3114 is supinating the patient's wrist 3116. Hand 3116 provides contact point 3118 at brachioradialis 3108. Patient 3120 is requested to extend elbow 3112 to the position shown in photograph 3104. Wrist 3116 is pronated at the end of the extension. This extension and pronation produces an internal sliding motion of the brachialis muscle with respect to contact point 3118. Contact point 3118 is drawn proximally during the extension to produce an external slide longitudinally along the brachioradialis muscle 3108.

EXAMPLE 10

TREATMENT OF THE WRIST AND FOREARM

ADHESIONS OF THE ULNAR NERVE AT THE FLEXOR CARPI ULNARIS

FIG. 20 includes a symptom pattern image 2016 showing that a patient is experiencing pain, numbness or tingling sensations on the skin of portions 2018 and 2020. Symptom pattern image 2016 is associated with indicator indicia 2022 identifying a plurality of treatment protocols including protocol '103.'

Figure 32:
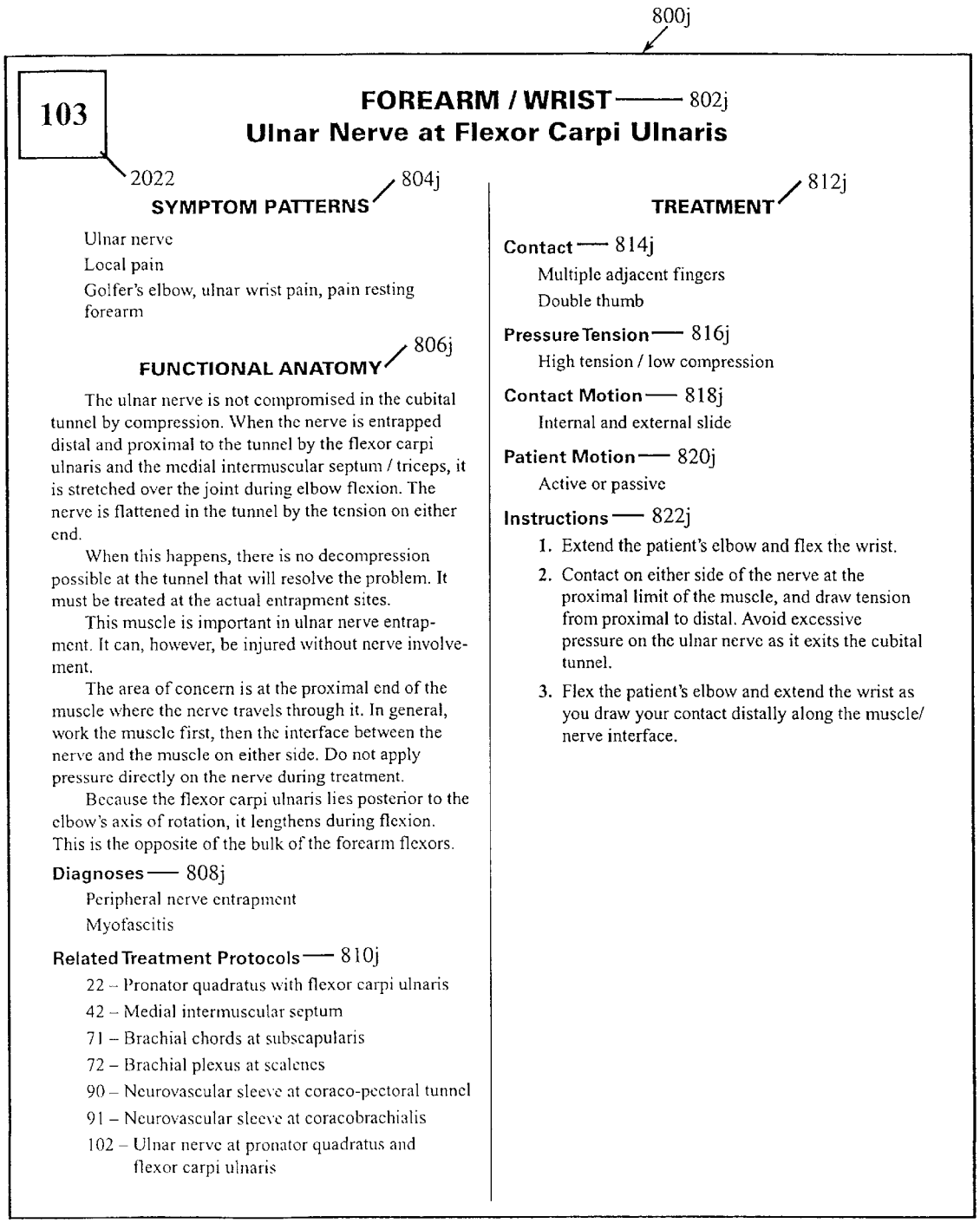
FIG. 32 depicts yet another treatment protocol for use in the FIG. 6 process corresponding to the FIG. 20 symptom pattern images.

FIG. 32 depicts treatment protocol '103,' which is designed to treat adhesions of the ulnar nerve at the flexor carpi ulnaris. This treatment protocol is most likely to be selected by people who have ulnar wrist pain, as well as local elbow, forearm and wrist pain when resting. The features of FIG. 32 are numbered in like manner with respect to features that are described above with respect to FIG. 8, except the features of FIG. 32 are provided with a "j" postscript to show that the corresponding indicia to which the features of FIG. 32 apply have been adapted to provide a treatment protocol for adhesions affecting the ulnar nerve at the flexor carpi ulnaris.

Figure 33:
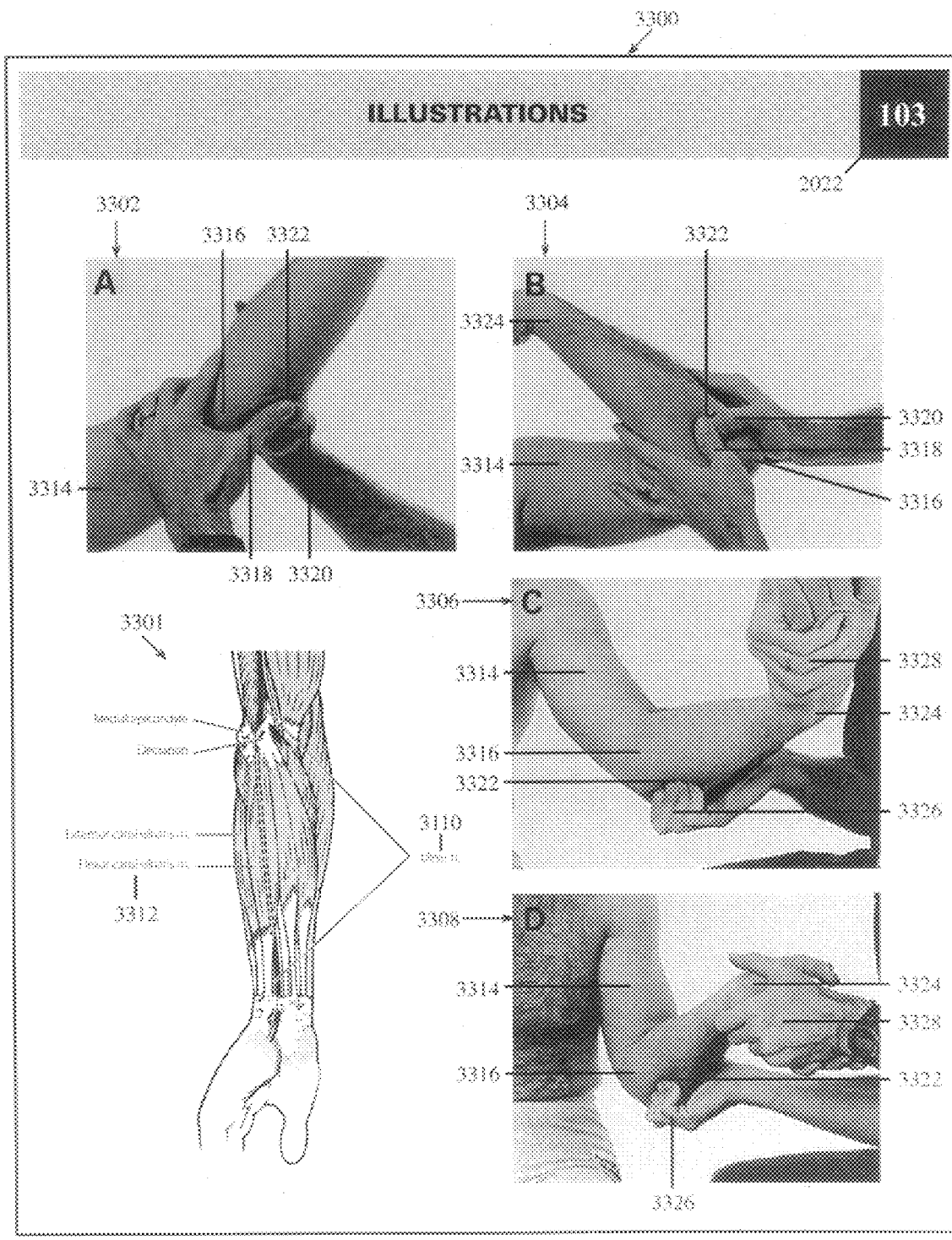
FIG. 33 depicts preferred features of the FIG. 30 treatment protocol.

FIG. 33 depicts indicia 3300 including an anatomical image 3301, as well as four photographs 3302, 3304, 3306, and 3308 showing soft tissue manipulation techniques for the features of anatomical image 3301. Anatomical image 3301 contains indicia annotating the features therein, e.g., ulnar nerve 3310 and flexor carpi ulnaris muscle 3312.

Photograph 3302 shows a seated patient's arm 3314 with elbow 3316 extended. Patient 3314 is requested to flex his or her wrist. Medical practitioner's thumbs 3318 and 3320 are placed one over the other to provide contact point 3322 on either side of the ulnar nerve at the proximal limit of the flexor carpi ulnaris muscle. Contact point 3322 and thumbs 3318 and 3320 are moved from proximal to distal while the patient extends wrist 3324 and flexes elbow 3316 to the position shown in photograph 3304. The patient's movement internally causes a longitudinal sliding motion of the ulnar nerve and the flexor carpi ulnaris with respect to contact point 3322. The movement of contact pont 3322 also occurs longitudinally with respect to the ulnar nerve and the flexor carpi ulnaris.

Photographs 3306 and 3308 show an alternative way of accomplishing the same longitudinal sliding motions produced by the contact and motions of photographs 3302 and 3304. Photograph 3306 shows the medical practitioner's fingers 3326 positioned to provide contact point 3326 and medical practitioner's hand 3328 positioned to assist flexion of patient's wrist 3324. The method of photographs 3306 and 3308 are better suited to passive flexion of elbow 3316, while the method of photographs 3302 and 3304 is better suited to active motion by patient 3314.

EXAMPLE 11

RESULTS ON ACTUAL PATIENTS

An expert medical practitioner diagnosed soft tissue adhesions in a total of 447 patients. The expert medical practitioner consulted anatomical diagrams to determine the best manner of performing the longitudinal massage techniques described with reference to FIG. 2 on each type of adhesion. The massage techniques significantly improved the symptoms of pain, burning, and tingling in fully 418 or 93.5% of these patients. The treatment protocols failed to produce significant improvement in 29 or 6.5% of these patients. An additional 10 patients were examined who required different therapy because their symptoms could not be treated with the massage techniques. An additional 18 patients could not be helped because they refused to comply with requests for them to assist with active motion in therapy.

The 418 successful treatments required an average of 6.2 office visits spaced at least two days apart. The 29 unsuccessful treatments required an average of 6.0 treatments before it was concluded that the treatments would not produce success. There appears to be no statistical significance based upon the treatment modality that was selected for use. That is, the statistics given above apply equally well to all treatment modalities or treatment protocols.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

We claim:

1. Apparatus for use in treating patients afflicted by soft tissue lesions according to an expert system treatment protocol, said apparatus comprising:

a plurality of symptom pattern images each of which provide an association between an anatomical image and an expert-derived symptom pattern, wherein said expert-derived symptom pattern images each include a depiction of a localized anatomical area where soft tissue lesions produce symptoms selected from the group consisting of numbness, tingling, pain, ache, burning, weakness, atrophy, circulatory changes, hypersensitivity, restricted motion, and combinations thereof;

means for storing said symptom pattern images;

a plurality of expert treatment protocols for the treatment of soft tissue lesions wherein each of said expert treatment protocols is a candidate for replicating symptoms corresponding to locations designated by said symptom pattern images, each of said treatment protocols including a depiction of longitudinal manipulation of soft tissues in concomitant with motion of a patient's body beneath a contact point placing subcutaneous tissues of the patient in tension while replicating symptoms corresponding to said symptom pattern images;

means for presenting said symptom pattern images to permit matching a patient's symptom pattern with at least one of said symptom pattern images;

means for associating selected ones of said expert treatment protocols with at least one of said symptom pattern images presented by said stored by said means for presenting said symptom pattern images; and means for retrieving one of said plurality of expert treatment protocols selected by said associating means to correspond with said at least one of said symptom pattern images during a course of treatment defined by said one of said plurality of expert treatment protocols.

2. The apparatus as set forth in claim 1 wherein said expert treatment protocols each include depictions of manual manipulation performed on an anatomical area of a patient, said anatomical area including said localized anatomical area of at least one of said symptom pattern images.

3. The apparatus as set forth in claim 1 wherein said expert treatment protocols each include depictions of an anatomical diagram of tissues underlying said anatomical area providing means for determining a proper contact point facilitating longitudinal motion of tissues beneath said contact point.

4. The apparatus as set forth in claim 1 wherein said expert treatment protocols each include an expert diagnosis of symptom patterns found in said expert symptom pattern images.

5. The apparatus as set forth in claim 4 wherein said expert treatment protocols include a list of symptoms associated with said expert diagnosis.

6. The apparatus as set forth in claim 1 wherein at least one of said expert treatment protocols includes a cross reference list of related treatment protocols associated with said at least one of said symptom pattern images.

7. The apparatus as set forth in claim 1 wherein said associating means includes each of said expert symptom pattern images having an identifier matching a corresponding identifier on a corresponding expert treatment protocol.

* * * * *

UNITED STATES PATENT AND TRADEMARK OFFICE
CERTIFICATE OF CORRECTION

| | |
|---|---|
| PATENT NO. | : 6,090,045 |
| APPLICATION NO. | : 08/807792 |
| DATED | : July 18, 2000 |
| INVENTOR(S) | : P. Michael Leahy and Tim Patterson |

Page 1 of 1

It is certified that error appears in the above-identified patent and that said Letters Patent is hereby corrected as shown below:

In column 1, lines 22 and 23, please delete:
"The present invention relates to the field of medical treatments for reducing the size and effect of various adhe-"
and insert the following:
-- The present invention relates to the field of health care for reducing the size and effect of various adhe- --

In column 1, lines 25 and 26, please delete:
"blood vessels, fascia, and nerves. More specifically, medical treatments according to the invention utilize an expert"
and insert the following:
-- blood vessels, fascia, and nerves. More specifically, treatment according to the invention utilizes an expert--

In column 7, lines 57 and 58, please delete:
"contact point. This technique is distinct from traditional massage techniques, which typically do not require patient"
and insert the following:
-- contact point. This technique is a unique massage system in comparison to traditional massage techniques, which typically do not require patient --

In column 7, line 62, please delete:
"manipulation, not massage. The working examples set forth"
and insert the following:
--manipulation of soft tissues of the body through pressure, tension, and movement. The working examples set forth --

Signed and Sealed this

Twenty-second Day of May, 2007

JON W. DUDAS
*Director of the United States Patent and Trademark Office*